(12) United States Patent
Li et al.

(10) Patent No.: US 12,064,633 B2
(45) Date of Patent: Aug. 20, 2024

(54) SENSING CARDIAC SIGNALS WITH LEADS IMPLANTED IN EPIDURAL SPACE

(71) Applicant: Medtronic, Inc., Minneapolis, MN (US)

(72) Inventors: Jiashu Li, Mounds View, MN (US); Jeffery Kramer, St. Louis Park, MN (US); Vinod Sharma, Maple Grove, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 18/192,536

(22) Filed: Mar. 29, 2023

(65) Prior Publication Data
US 2023/0233861 A1    Jul. 27, 2023

Related U.S. Application Data

(63) Continuation of application No. 17/067,231, filed on Oct. 9, 2020, now Pat. No. 11,642,531.

(51) Int. Cl.
*A61N 1/36* (2006.01)
*A61B 5/00* (2006.01)
(Continued)

(52) U.S. Cl.
CPC ...... *A61N 1/36139* (2013.01); *A61B 5/02405* (2013.01); *A61B 5/366* (2021.01);
(Continued)

(58) Field of Classification Search
None
See application file for complete search history.

(56) References Cited

U.S. PATENT DOCUMENTS 5,233,984 A * 8/1993 Thompson ............... G01C 9/20
607/18
7,775,993 B2    8/2010 Heruth et al.
(Continued)

FOREIGN PATENT DOCUMENTS

| WO | 2010088539 A1 | 8/2010 |
| WO | 2019122903 A2 | 6/2019 |
| WO | 2020223165 A1 | 11/2020 |

OTHER PUBLICATIONS

Extended Search Report from counterpart European Application No. 21197799.6, dated Mar. 9, 2022, 7 pp.
(Continued)

*Primary Examiner* — Ankit D Tejani
(74) *Attorney, Agent, or Firm* — Shumaker & Sieffert, P.A.

(57) ABSTRACT

Techniques are disclosed for using a cardiac signal sensed via a plurality of electrodes disposed on one or more leads implanted within an epidural space of a patient to control spinal cord stimulation (SCS) therapy. In one example, an implantable medical device (IMD) senses an electrical signal via a plurality of electrodes disposed on one or more leads implanted within an epidural space of a patient. Processing circuitry determines, from the electrical signal, one or more cardiac features indicative of activity of a heart of the patient. The processing circuitry controls, based on the one or more cardiac features, delivery of SCS therapy to the patient.

20 Claims, 9 Drawing Sheets

(51) Int. Cl.
*A61B 5/024* (2006.01)
*A61B 5/366* (2021.01)

(52) U.S. Cl.
CPC .............. *A61B 5/686* (2013.01); *A61B 5/725* (2013.01); *A61N 1/36062* (2017.08)

(56) References Cited

U.S. PATENT DOCUMENTS

| | | |
|---|---|---|
| 8,055,348 B2 | 11/2011 | Heruth et al. |
| 8,332,038 B2 | 12/2012 | Heruth et al. |
| 2005/0209512 A1 | 9/2005 | Heruth et al. |
| 2009/0270960 A1 | 10/2009 | Zhao et al. |
| 2010/0274106 A1 | 10/2010 | Heruth et al. |
| 2014/0277278 A1 | 9/2014 | Keel et al. |
| 2018/0133480 A1 | 5/2018 | Annoni et al. |
| 2018/0192941 A1* | 7/2018 | Annoni .............. A61N 1/37264 |
| 2020/0147391 A1* | 5/2020 | Moffitt .................. A61N 1/025 |
| 2022/0111211 A1 | 4/2022 | Li et al. |

OTHER PUBLICATIONS

Prosecution History from U.S. Appl. No. 17/067,231, dated Jun. 30, 2022 through Jan. 25, 2023, 38 pp.
Response to Search Report from counterpart European Application No. 21197799.6, dated Oct. 12, 2022, 16 pp.
Extended Search Report from counterpart European Application No. 23191378.1 dated Nov. 23, 2023, 8 pp.
Response to Extended Search Report dated Nov. 23, 2023, from counterpart European Application No. 23191378.1 filed Jun. 11, 2024, 15 pp.

* cited by examiner

SENSING CARDIAC SIGNALS WITH LEADS IMPLANTED IN EPIDURAL SPACE

This application is a continuation application claiming priority to U.S. patent application Ser. No. 17/067,231, filed Oct. 9, 2020, the entire contents of which is incorporated herein by reference.

TECHNICAL FIELD

This disclosure generally relates to electrical stimulation therapy.

BACKGROUND

Medical devices may be external or implanted, and may be used to deliver electrical stimulation therapy to various tissue sites of a patient to treat a variety of symptoms or conditions such as chronic pain, tremor, Parkinson's disease, epilepsy, urinary or fecal incontinence, sexual dysfunction, obesity, gastroparesis, visceral disorders, cognitive disorders, and movement disorders. A medical device may deliver electrical stimulation therapy via one or more electrodes located proximate to target locations associated with the brain, the spinal cord, pelvic nerves, peripheral nerves, or the gastrointestinal tract of a patient. Electrodes may be deployed, for example, on implantable leads and/or implantable device housings. Electrical stimulation may be used in different therapeutic applications, such as deep brain stimulation (DBS), spinal cord stimulation (SCS), pelvic floor stimulation, tibial nerve stimulation, gastric stimulation, or peripheral nerve field stimulation (PNFS).

A clinician may select values for a number of programmable parameters in order to define the electrical stimulation therapy to be delivered by the implantable stimulator to a patient. For example, the clinician may select one or more electrodes, a polarity of each selected electrode, a voltage or current amplitude, a recharge interval, a pulse width, a pulse frequency, and/or an inter-stimulation interval as stimulation parameters. One or more parameters of the electrical stimulation therapy, such as electrode combination, electrode polarity, amplitude, pulse width, pulse rate, and duty cycle define the electrical stimulation therapy to be delivered to the patient.

SUMMARY

In general, the disclosure describes devices, systems, methods, and techniques for obtaining a cardiac signal from an electrical signal sensed via a plurality of electrodes disposed on one or more leads implanted within an epidural space of a patient to control spinal cord stimulation (SCS) therapy. The cardiac signal may be indicative of pain or uncomfortable sensations experienced by the patient, which in turn may be indicative of the efficacy of the SCS therapy. In one example, an implantable medical device (IMD) delivers, via electrodes disposed on a lead implanted within an epidural space of a patient, SCS therapy to the patient. The IMD senses, via the electrodes disposed on the lead implanted within the epidural space of the patient, an electrical signal from the patient. The IMD may process the electrical signal to obtain a cardiac signal of a heart of the patient from the electrical signal and obtains one or more cardiac features from the cardiac signal. Example cardiac features may include a heart rate variability (HRV) of the heart of the patient, a root mean square of successive differences between normal heartbeats (RMSSD) of the heart of the patient, QRS and QT intervals (which are indicative of depolarization and repolarization of the heart) or frequency domain information of the heart rate of the patient. One or more cardiac features present within the cardiac signal may be indicative of pain experienced by the patient and may be used as a biomarker to control delivery of SCS therapy. In some examples, the IMD may further sense an evoked compound action potential (ECAP) responsive to the SCS stimulation. The IMD can control SCS therapy delivery based on the cardiac features and, in some examples, ECAP data. For example, the IMD can adjust one or more parameters at least partially defining the SCS therapy or cycle stimulation on and off to control delivery of SCS stimulation.

The techniques of the disclosure may provide specific improvements to the field of SCS therapy that have practical applications. For example, the techniques disclosed herein may enable a system to use cardiac activity as a biomarker for pain experienced by the patient to control electrical stimulation therapy. Furthermore, the techniques disclosed herein may be used in conjunction with the sensing of ECAP signals so as to provide increased granularity of closed-loop control of electrical stimulation therapy parameters, thereby increasing the efficacy of electrical stimulation therapy on a patient-specific basis as well as increasing the efficiency of energy consumption by the IMD.

In one example, this disclosure describes a method comprising: sensing, by an implantable medical device (IMD) and via a plurality of electrodes disposed on one or more leads implanted within an epidural space of a patient, an electrical signal; determining, by processing circuitry and from the electrical signal, one or more cardiac features indicative of activity of a heart of the patient; and controlling, by the processing circuitry and based on the one or more cardiac features, delivery of spinal cord stimulation (SCS) therapy to the patient.

In another example, this disclosure describes a medical device comprising processing circuitry configured to: receive an electrical signal sensed via a plurality of electrodes disposed on one or more leads implanted within an epidural space of a patient; determine, from the electrical signal, one or more cardiac features indicative of electrical activity of a heart of the patient; and control, based on the one or more cardiac features, delivery of spinal cord stimulation (SCS) therapy to the patient.

In another example, this disclosure describes a system comprising: an implantable medical device comprising: a plurality of electrodes disposed on one or more leads configured for implantation within an epidural space of a patient; sensing circuitry configured to sense, via the plurality of electrodes, an electrical signal; and stimulation generation circuitry configured to deliver, via the plurality of electrodes, spinal cord stimulation (SCS) therapy to the patient; and processing circuitry configured to: determine, from the electrical signal, one or more cardiac features indicative of electrical activity of a heart of the patient; and control, based on the one or more cardiac features, the stimulation generation circuitry to deliver the SCS therapy to the patient.

The details of one or more examples of the techniques of this disclosure are set forth in the accompanying drawings and the description below. Other features, objects, and advantages of the techniques will be apparent from the description and drawings, and from the claims.

configured to deliver spinal cord stimulation (SCS) therapy and an external programmer, in accordance with one or more techniques of this disclosure.

Figure 1:
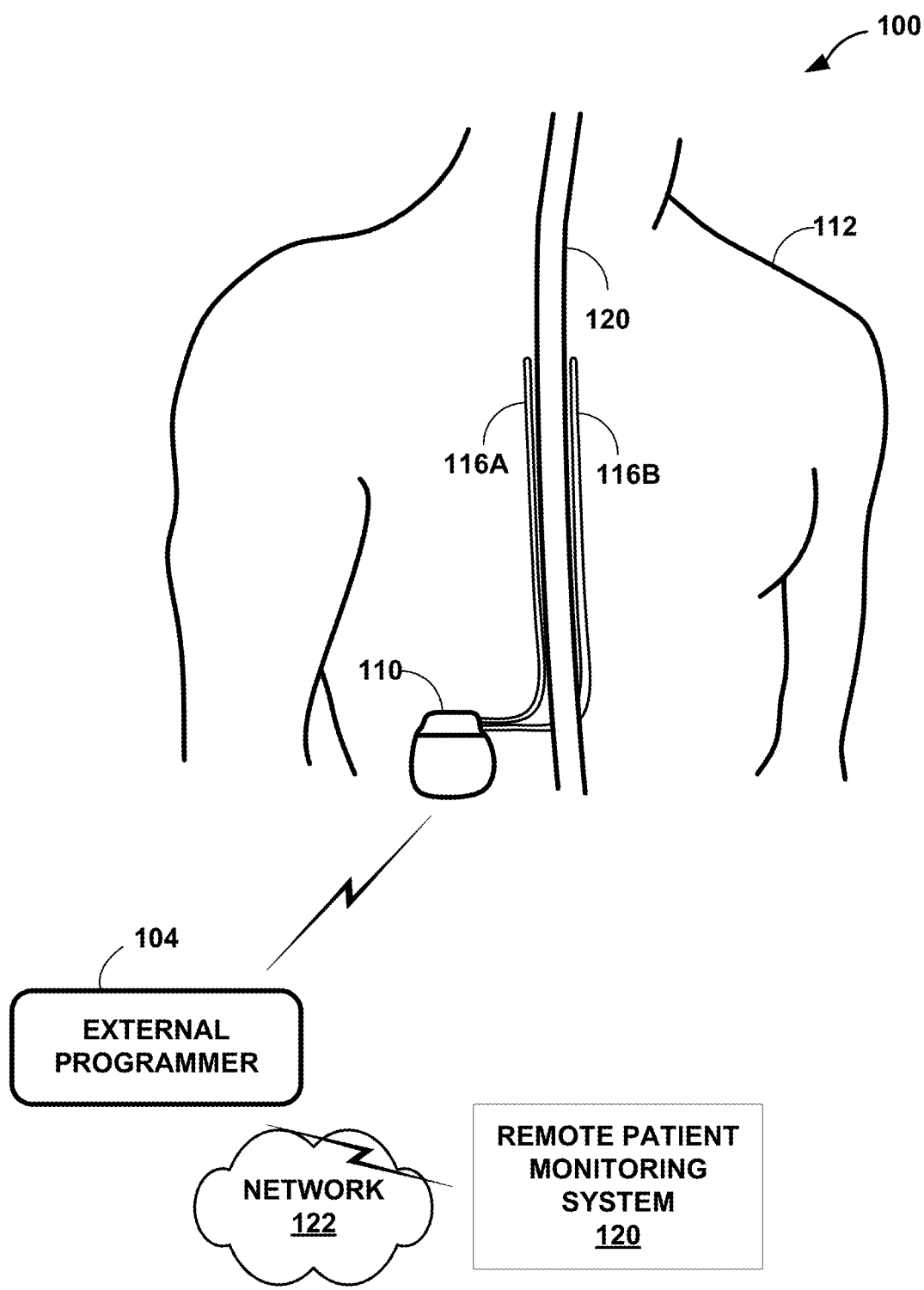
FIG. 1 is a conceptual diagram illustrating an example system that includes an implantable medical device (IMD)
Figure 2:
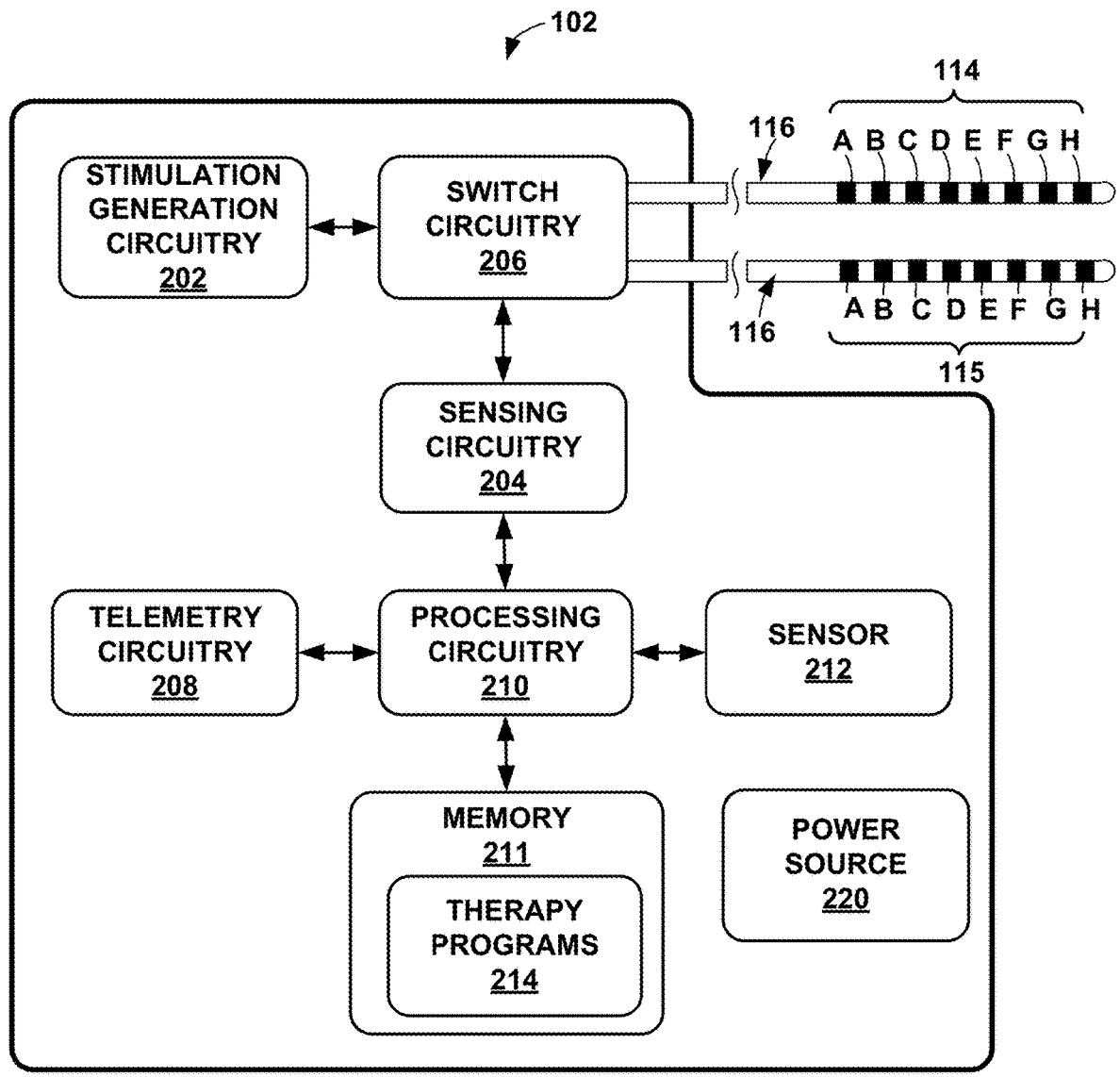

FIG. 2 is a block diagram of the example IMD of FIG. 1.

Figure 3:
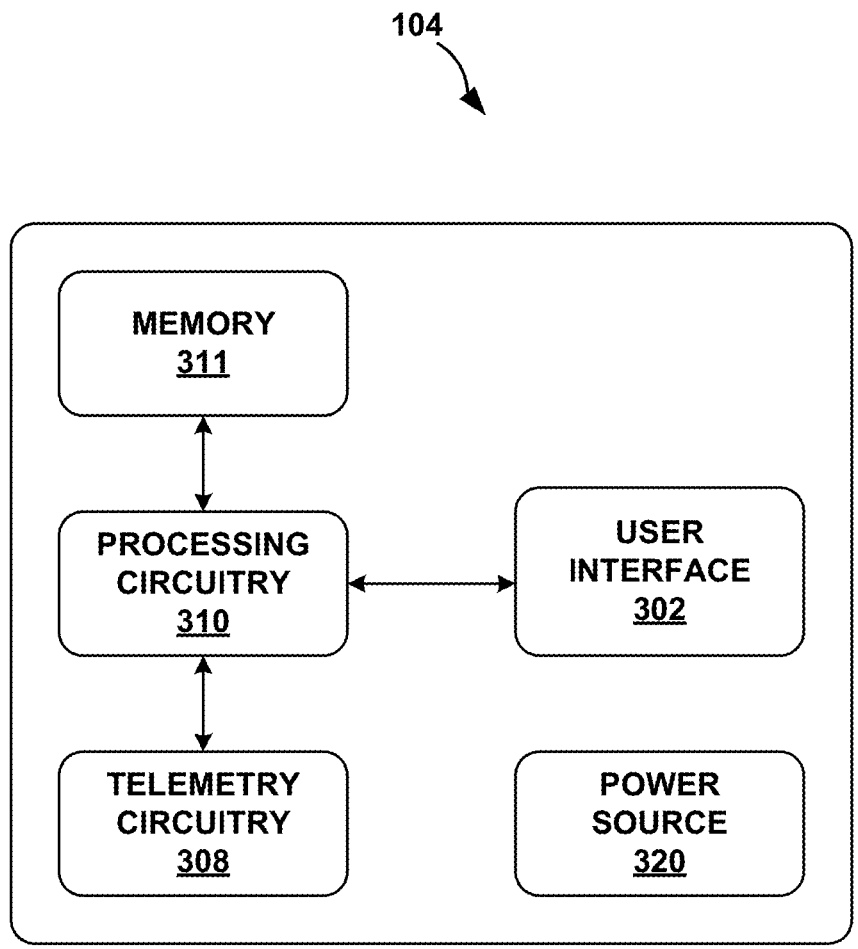

FIG. 3 is a block diagram of the example external programmer of FIG. 1.

Figure 4:
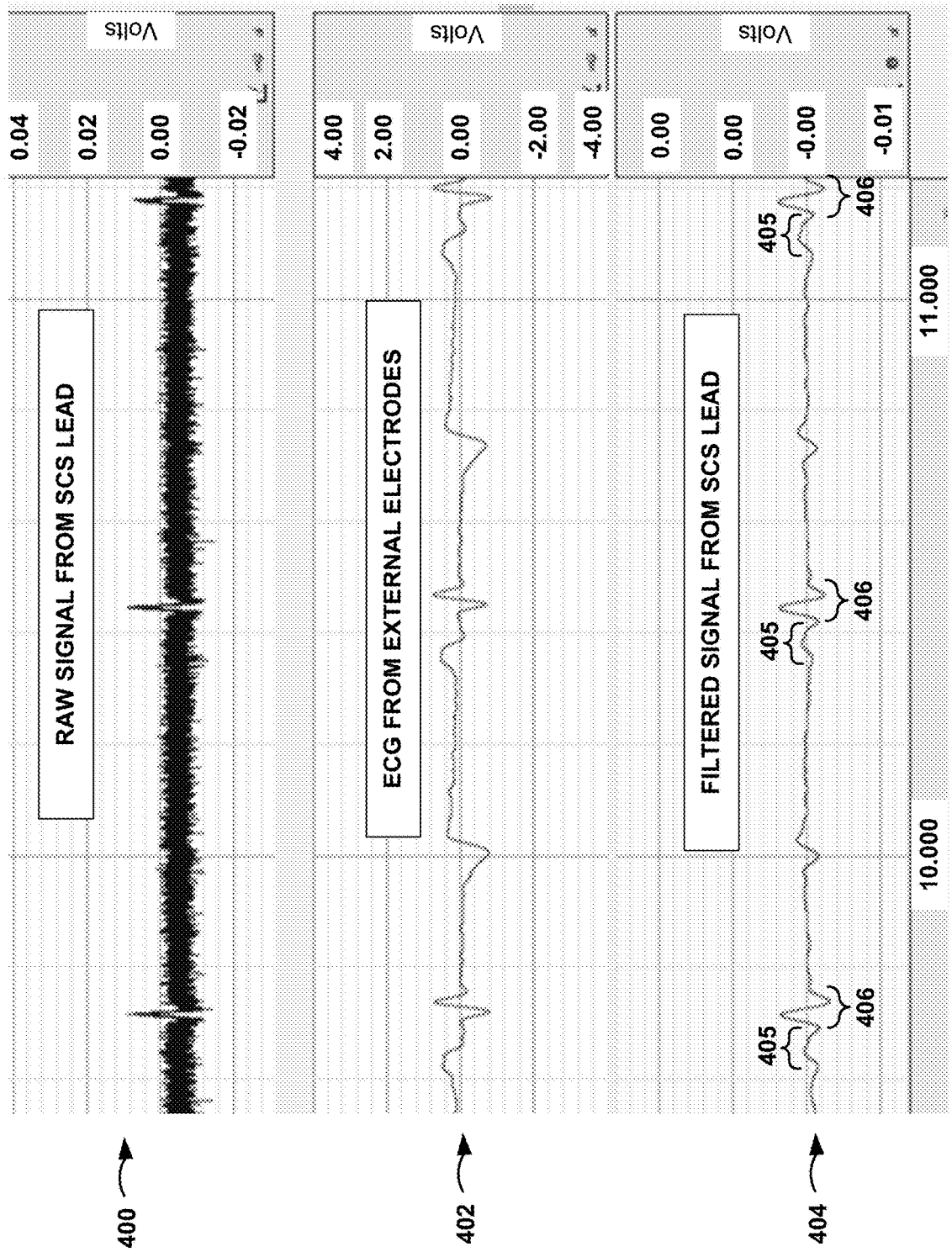

FIG. 4 is a graph illustrating example signals sensed in accordance with the techniques of the disclosure.

Figure 5:
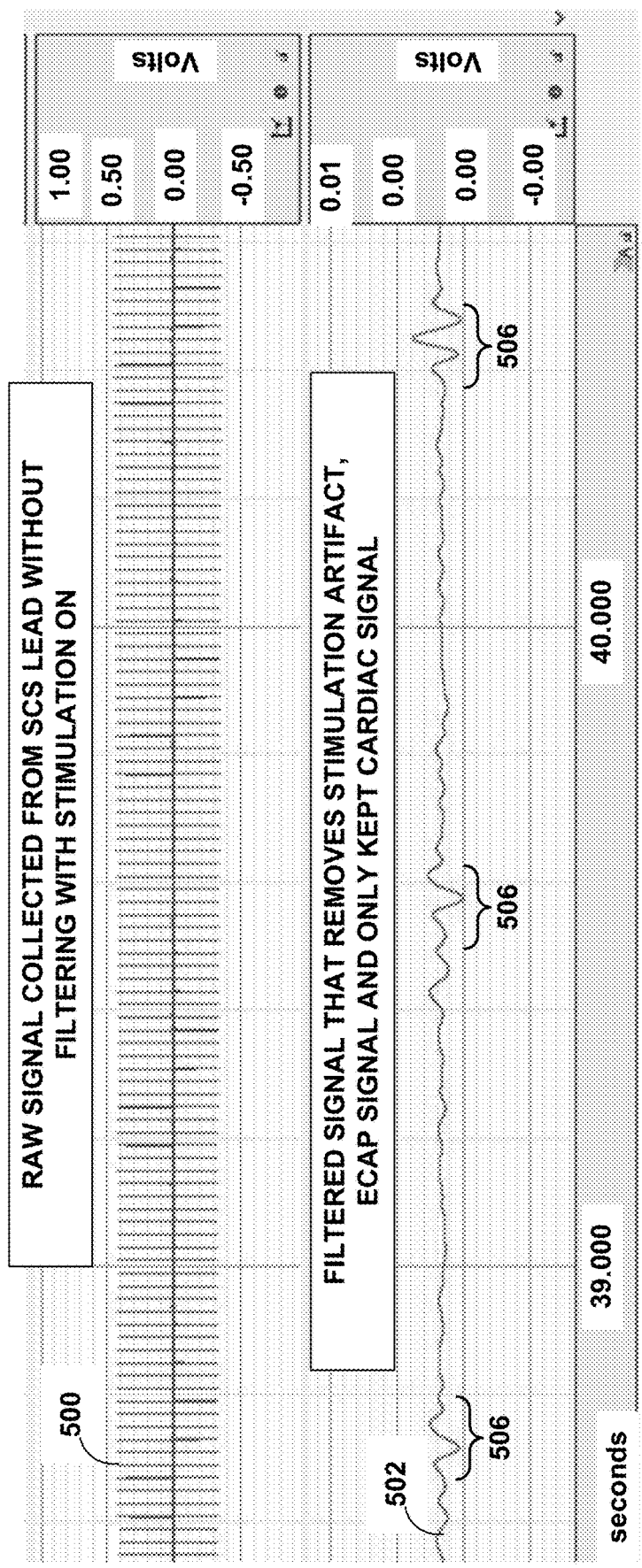

FIG. 5 is a graph illustrating example signals sensed in accordance with the techniques of the disclosure.

Figure 6:
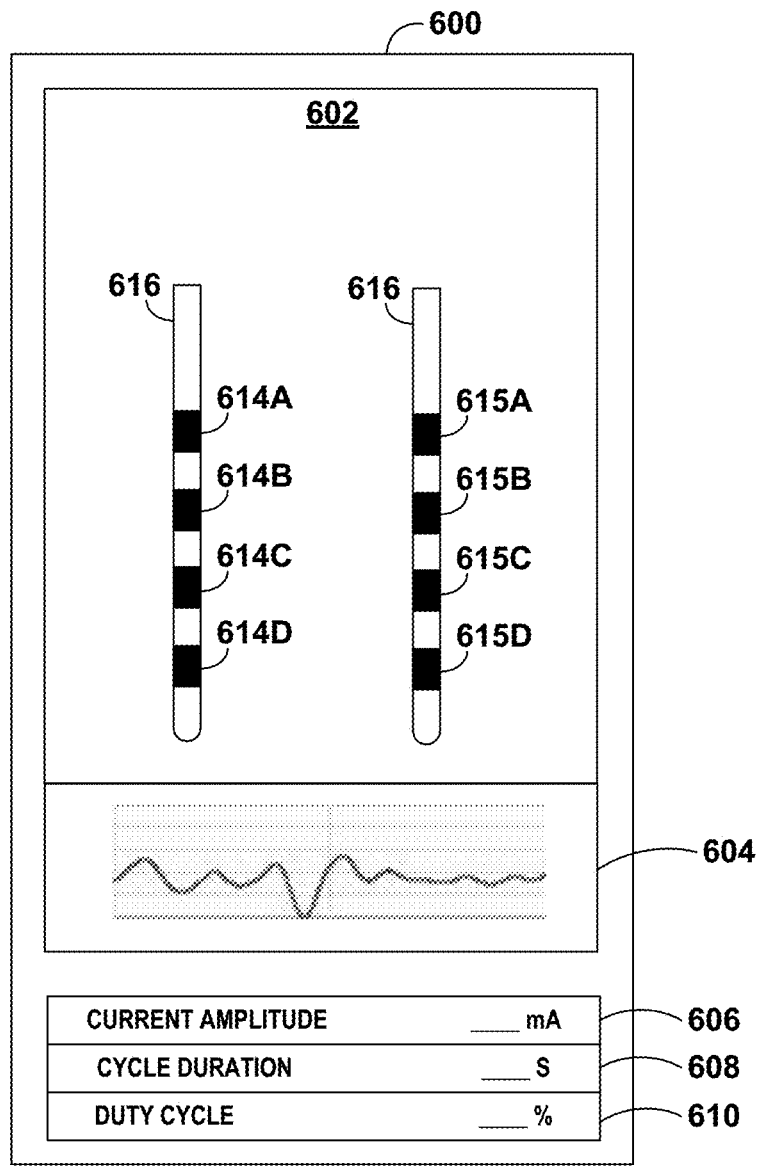

FIG. 6 is an illustration of an example user interface in accordance with the techniques of the disclosure.

Figure 7A:
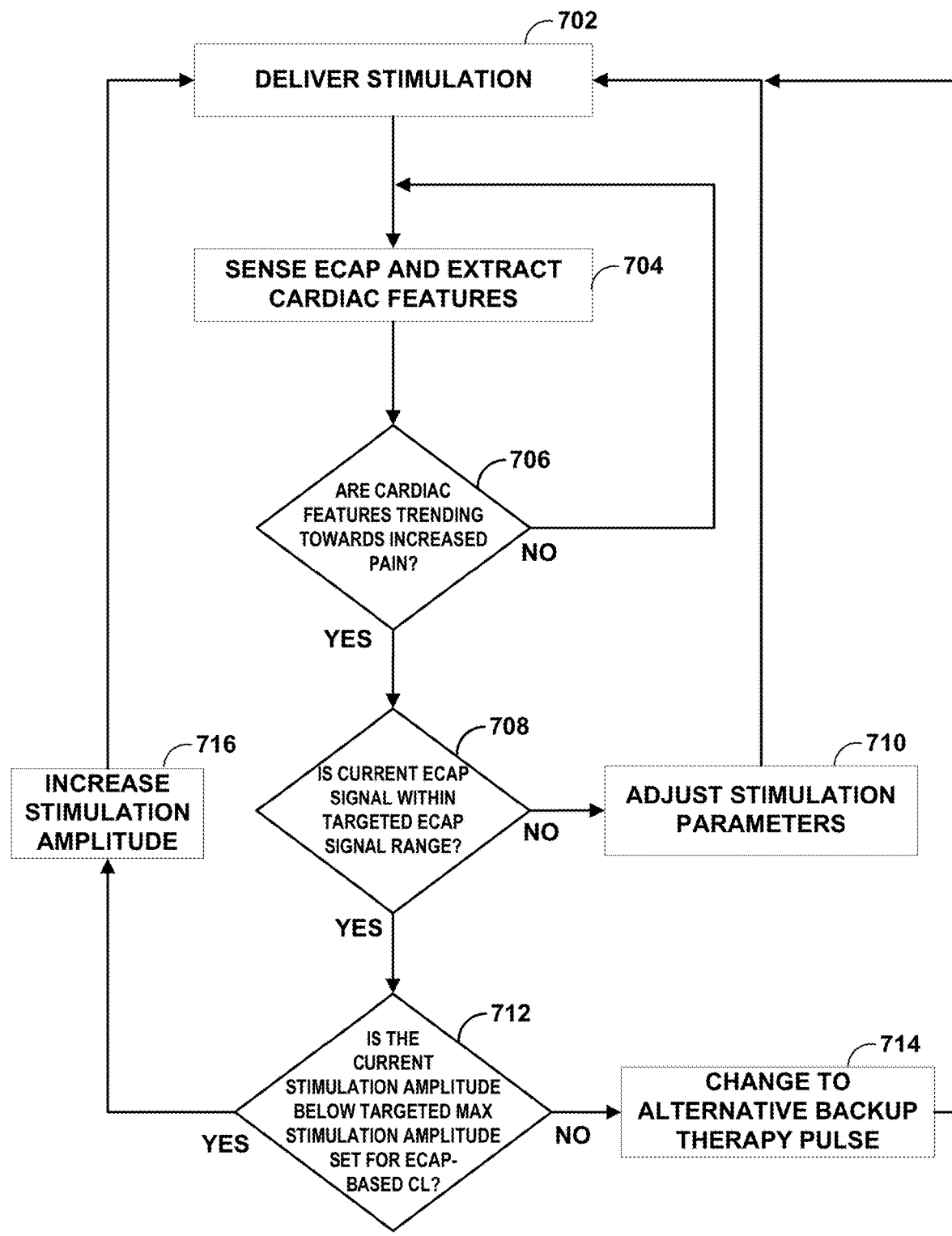
Figure 7B:
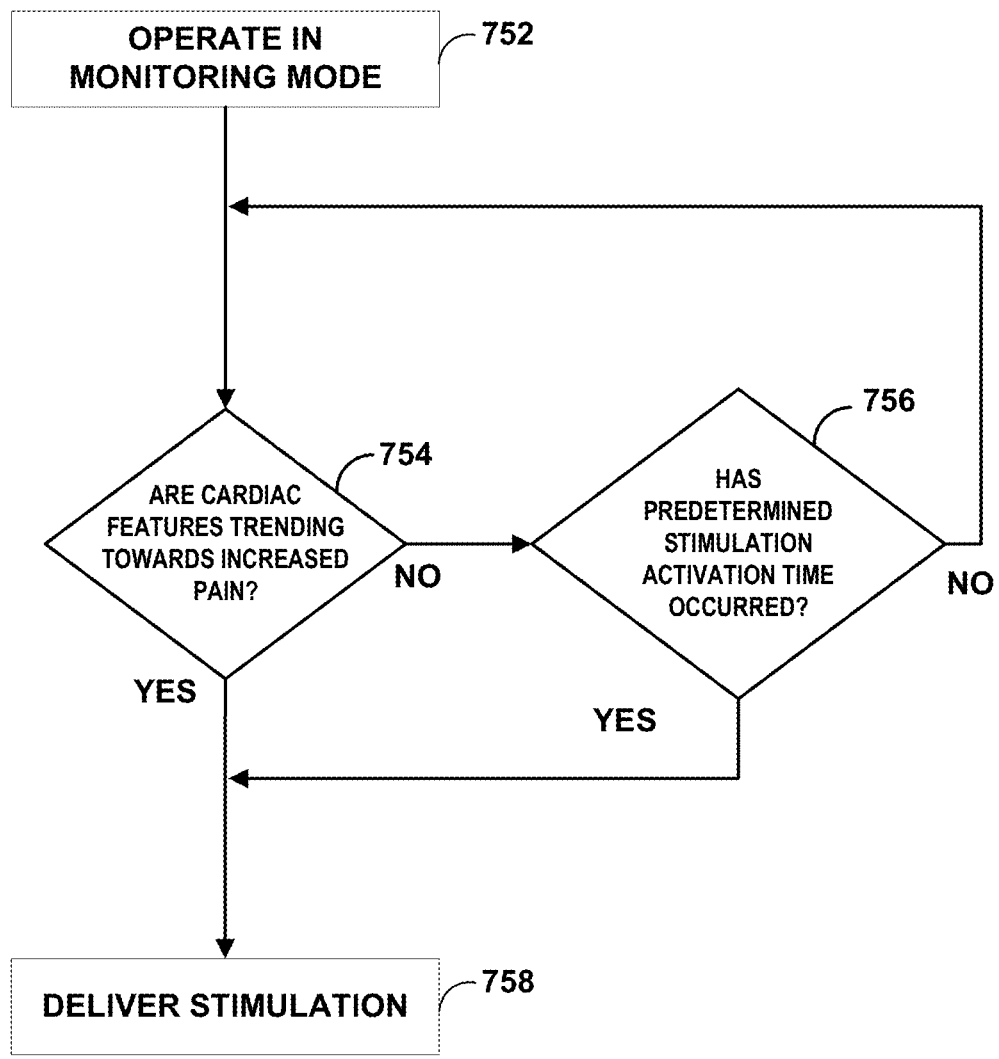

FIGS. 7A-7B are flowcharts illustrating an example operation in accordance with the techniques of the disclosure.

Figure 8:
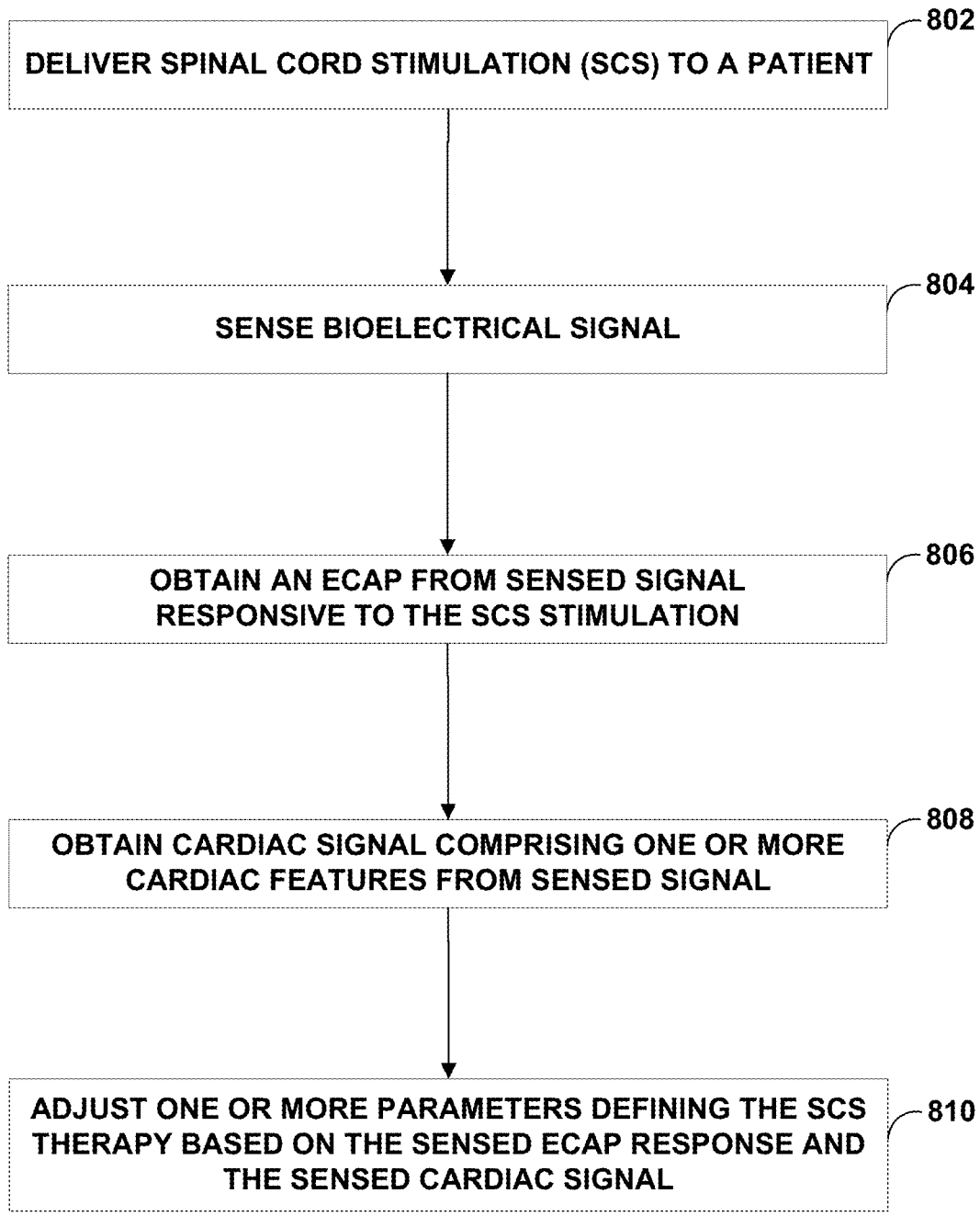

FIG. 8 is a flowchart illustrating an example operation in accordance with the techniques of the disclosure.

Like reference characters refer to like elements throughout the figures and description.

DETAILED DESCRIPTION

In accordance with the techniques of the disclosure, a medical system as described herein delivers SCS therapy using closed loop modulation with recorded cardiac features, such as heart rate, obtained from electrical signals sensed via an implanted SCS lead. Medical devices may use therapy cycling (e.g., cycling between periods of time of where electrical stimulation therapy is delivered and periods of time where electrical stimulation therapy is not delivered) to reduce a total amount of energy used while providing patient therapy. An SCS system may sense electrical signals, such as evoked compound action potentials (ECAPs), using electrodes carried by a lead implanted in the epidural space next to the spinal cord. Typically, an SCS system filters out or ignores noise or other features (e.g., cardiac signals, such as heart rate) other than the desired sensed signal. Therefore, such systems can identify and focus on ECAP detection to implement closed-loop SCS therapy. Systems detecting ECAPs can implement cycling as a technique to provide SCS therapy with predetermined periods of "on" and "off" time (e.g., where stimulation is delivered and not delivered, respectively). However, in order to employ ECAPs as a biomarker to control therapy cycling, stimulation pulses having an amplitude sufficiently large to elicit a recordable ECAP muse be provided by the implanted SCS lead. Since stimulation pulses are required to detect ECAPs in an ECAP-based closed loop system for therapy cycling, no ECAPs can be detected during the "off" state of the therapy cycle. Alternatively, stimulus pulses must be delivered during the "off" state, which may confuse the patient if the stimulus pulses can be felt. Moreover, ECAPs are indicative of a strength of the delivered stimulus and can be used to modulate stimulation intensity. However, the ECAPs are not directly indicative of therapy efficacy or symptoms perceived by the patient such as pain.

A clinician can program the therapy cycle duration and duty cycle of the SCS therapy in a clinical setting. The settings chosen by the clinician in a clinic may not be the most energy efficient or may not provide the most effective therapy to the patient because a symptom, such as pain, experienced by the patient may be affected by various factors and can change from day to day. Furthermore, for the medical system to perform precisely, the clinician may be required to spend a long period of time manually titrating the stimulation and cycling parameters to achieve efficacious and efficient therapy. Such a system still may not be effective for all subjects due to varied pain amongst patients as well as differing factors that can induce pain.

In accordance with the techniques of the disclosure, a medical device system may process electrical signals sensed by electrodes of implanted SCS leads to obtain a cardiac signal comprising one or more cardiac features indicative of activity of a heart of the patient. Upon initial programming, a clinician or the system may adjust electrical stimulation therapy parameters based on a periodically computed HRV for better therapy titration, and may monitor characteristic values of ECAPs to adjust stimulation parameter values and/or limit the electrical stimulation therapy parameters (e.g., stimulation amplitude) from reaching a level at which the patient experiences discomfort. Using the obtained cardiac signal, the medical device system may identify one or more cardiac features, such as time domain information including HRV, RMSSD, as well as frequency domain information that reflects cardiac activity and/or sympathetic and parasympathetic function. The medical device system may use these cardiac features as pain biomarkers that represent symptoms experienced by the patient and track such cardiac features as a measure of the efficacy of SCS therapy delivered to the patient. For example, a medical device may cycle stimulation (e.g., turn on stimulation) prior to a predetermined time if, e.g., an HRV of the patient has decreased or if another sensed pain biomarker signal indicates a shift towards overall increase of pain. As described herein, a system may employ one or more cardiac features, such as a heart rate, extracted from an electrical signal sensed from electrodes of the SCS leads in conjunction with characteristic values of ECAP signals to implements a closed loop SCS delivery system (e.g., control stimulation). A medical device system as described can, in some examples, combines both ECAPs and cardiac signals to control patient-specific therapy in order to improve therapeutic benefit and reduce energy consumption.

FIG. 1 is a conceptual diagram illustrating an example system 100 that includes an implantable medical device (IMD) 110 configured to deliver spinal cord stimulation (SCS) therapy and an external programmer 104, in accordance with one or more techniques of this disclosure. Although the techniques described in this disclosure are generally applicable to a variety of medical devices including external devices and IMDs, application of such techniques to IMDs and, more particularly, implantable electrical stimulators (e.g., neurostimulators) will be described for purposes of illustration. More particularly, the disclosure will refer to an implantable SCS system for purposes of illustration, but without limitation as to other types of medical devices or other therapeutic applications of medical devices.

As shown in FIG. 1, system 100 includes an IMD 110, leads 116A and 116B (collectively, "leads 116"), and external programmer 104 shown in conjunction with a patient 112, who is ordinarily a human patient. In the example of FIG. 1, IMD 110 is an implantable electrical stimulator that is configured to generate and deliver electrical stimulation therapy to patient 112 via one or more electrodes of electrodes of leads 116, e.g., for relief of chronic pain or other symptoms. In other examples, IMD 110 may be coupled to a single lead carrying multiple electrodes or more than two leads each carrying multiple electrodes. In some examples, the stimulation signals, or pulses, may be configured to elicit detectable ECAP signals that IMD 110 may use to determine the posture state occupied by patient 112 and/or determine how to adjust one or more parameters that define stimulation therapy. IMD 110 may be a chronic electrical stimulator that remains implanted within patient 112 for weeks, months, or even years. In other examples, IMD 110 may be a temporary, or trial, stimulator used to screen or evaluate the efficacy of electrical stimulation for chronic therapy. In one example, IMD 110 is implanted within patient 112, while in another example, IMD 110 is an external device coupled to percutaneously implanted leads. In some examples, IMD 110 uses one or more leads, while in other examples, IMD 110 is leadless.

IMD 110 may be constructed of any polymer, metal, or composite material sufficient to house the components of IMD 110 (e.g., components illustrated in FIG. 2) within patient 112. In this example, IMD 110 may be constructed with a biocompatible housing, such as titanium or stainless steel, or a polymeric material such as silicone, polyurethane, or a liquid crystal polymer, and surgically implanted at a site in patient 112 near the pelvis, abdomen, or buttocks. In other examples, IMD 110 may be implanted within other suitable sites within patient 112, which may depend, for example, on the target site within patient 112 for the delivery of electrical stimulation therapy. The outer housing of IMD 110 may be configured to provide a hermetic seal for components, such as a rechargeable or non-rechargeable power source. In addition, in some examples, the outer housing of IMD 110 is selected from a material that facilitates receiving energy to charge the rechargeable power source.

Electrical stimulation energy, which may be constant current or constant voltage-based pulses, for example, is delivered from IMD 110 to one or more target tissue sites of patient 112 via one or more electrodes (not shown) of implantable leads 116. In the example of FIG. 1, leads 116 carry electrodes that are placed adjacent to the target tissue of spinal cord 120. One or more of the electrodes may be disposed at a distal tip of one of leads 116 and/or at other positions at intermediate points along the lead. Leads 116 may be implanted and coupled to IMD 110. The electrodes may transfer electrical stimulation generated by an electrical stimulation generator in IMD 110 to tissue of patient 112. Although leads 116 may each be a single lead, leads 116 may include a lead extension or other segments that may aid in implantation or positioning of leads 116. In some other examples, IMD 110 may be a leadless stimulator with one or more arrays of electrodes arranged on a housing of the stimulator rather than leads that extend from the housing. In addition, in some other examples, system 100 may include one lead or more than two leads, each coupled to IMD 110 and directed to similar or different target tissue sites.

The electrodes of leads 116 may be electrode pads on a paddle lead, circular (e.g., ring) electrodes surrounding the body of the lead, conformable electrodes, cuff electrodes, segmented electrodes (e.g., electrodes disposed at different circumferential positions around the lead instead of a continuous ring electrode), any combination thereof (e.g., ring electrodes and segmented electrodes) or any other type of electrodes capable of forming unipolar, bipolar or multipolar electrode combinations for therapy. Ring electrodes arranged at different axial positions at the distal ends of leads 116 will be described for purposes of illustration.

The deployment of electrodes via leads 116 is described for purposes of illustration, but arrays of electrodes may be deployed in different ways. For example, a housing associated with a leadless stimulator may carry arrays of electrodes, e.g., rows and/or columns (or other patterns), to which shifting operations may be applied. Such electrodes may be arranged as surface electrodes, ring electrodes, or protrusions. As a further alternative, electrode arrays may be formed by rows and/or columns of electrodes on one or more paddle leads. In some examples, electrode arrays include electrode segments, which are arranged at respective positions around a periphery of a lead, e.g., arranged in the form of one or more segmented rings around a circumference of a cylindrical lead. In other examples, one or more of leads 116 are linear leads having 8 ring electrodes along the axial length of the lead. In another example, the electrodes are segmented rings arranged in a linear fashion along the axial length of the lead and at the periphery of the lead.

The stimulation parameter set of a therapy stimulation program that defines the stimulation pulses of electrical stimulation therapy by IMD 110 through the electrodes of leads 116 may include information identifying which electrodes have been selected for delivery of stimulation according to a stimulation program, the polarities of the selected electrodes, i.e., the electrode combination for the program, voltage or current amplitude, pulse frequency, pulse width, pulse shape of stimulation delivered by the electrodes. These stimulation parameters values that make up the stimulation parameter set that defines pulses may be predetermined parameter values defined by a user and/or automatically determined by system 100 based on one or more factors or user input.

If control pulses separate from the informed pulses (together different types of stimulation pulses) used for therapy are needed to elicit a detectable ECAP signal, system 100 may employ an ECAP test stimulation program that defines stimulation parameter values that define control pulses delivered by IMD 110 through at least some of the electrodes of leads 116. These stimulation parameter values may include information identifying which electrodes have been selected for delivery of control pulses, the polarities of the selected electrodes, i.e., the electrode combination for the program, and voltage or current amplitude, pulse frequency, pulse width, and pulse shape of stimulation delivered by the electrodes. The stimulation signals (e.g., one or more stimulation pulses or a continuous stimulation waveform) defined by the parameters of each ECAP test stimulation program are configured to evoke a compound action potential from nerves. In some examples, the ECAP test stimulation program defines when the control pulses are to be delivered to the patient based on the frequency and/or pulse width of the informed pulses. However, the stimulation defined by each ECAP test stimulation program are not intended to provide or contribute to therapy for the patient. In addition, the ECAP test stimulation program may define the control pulses used for each sweep of pulses that are used to determine the posture state of the patient.

Although FIG. 1 is directed to SCS therapy, e.g., used to treat pain, in other examples system 100 may be configured to treat any other condition that may benefit from electrical stimulation therapy. For example, system 100 may be used to treat tremor, Parkinson's disease, epilepsy, a pelvic floor disorder (e.g., urinary incontinence or other bladder dysfunction, fecal incontinence, pelvic pain, bowel dysfunction, or sexual dysfunction), obesity, gastroparesis, or psychiatric disorders (e.g., depression, mania, obsessive compulsive disorder, anxiety disorders, and the like). In this manner, system 100 may be configured to provide therapy taking the form of deep brain stimulation (DBS), peripheral nerve stimulation (PNS), peripheral nerve field stimulation (PNFS), cortical stimulation (CS), pelvic floor stimulation, tibial nerve stimulation, gastrointestinal stimulation, or any other stimulation therapy capable of treating a condition of patient 112.

In some examples, leads 116 include one or more sensors configured to allow IMD 110 to monitor one or more parameters of patient 112, such as patient activity, temperature, tissue blood perfusion, or other characteristics. The one or more sensors may be provided in addition to, or in place of, therapy delivery by leads 116.

IMD 110 is configured to deliver electrical stimulation therapy to patient 112 via selected combinations of electrodes carried by one or both of leads 116, alone or in combination with an electrode carried by or defined by an outer housing of IMD 110. The target tissue for the electrical stimulation therapy may be any tissue affected by electrical stimulation, which may be in the form of electrical stimulation pulses or continuous waveforms. In some examples, the target tissue includes nerves, smooth muscle or skeletal muscle. In the example illustrated by FIG. 1, the target tissue is tissue proximate to the spinal cord 120, such as within an intrathecal space or epidural space of spinal cord 120, or, in some examples, adjacent nerves that branch off spinal cord 120. Leads 116 may be introduced into spinal cord 120 in via any suitable region, such as the thoracic, cervical or lumbar regions. Stimulation of spinal cord 120 may, for example, prevent pain signals from traveling through spinal cord 120 and to the brain of patient 112. Patient 112 may perceive the interruption of pain signals as a reduction in pain and, therefore, efficacious therapy results. In other examples, stimulation of spinal cord 120 may produce paresthesia which may be reduce the perception of pain by patient 112, and thus, provide efficacious therapy results.

IMD 110 is configured to generate and deliver electrical stimulation therapy to a target stimulation site within patient 112 via the electrodes of leads 116 to patient 112 according to one or more therapy stimulation programs. A therapy stimulation program defines values for one or more parameters (e.g., a parameter set) that define an aspect of the therapy delivered by IMD 110 according to that program. For example, a therapy stimulation program that controls delivery of stimulation by IMD 110 in the form of pulses may define values for voltage or current pulse amplitude, pulse width, pulse rate (e.g., pulse frequency), electrode combination, pulse shape, etc. for stimulation pulses delivered by IMD 110 according to that program.

Furthermore, IMD 110 may be configured to deliver control stimulation to patient 112 via a combination of electrodes of leads 116, alone or in combination with an electrode carried by or defined by an outer housing of IMD 110 in order to detect ECAP signals (e.g., control pulses and/or informed pulses). The tissue targeted by the stimulation may be the same or similar tissue targeted by the electrical stimulation therapy, but IMD 110 may deliver stimulation pulses for ECAP signal detection via the same, at least some of the same, or different electrodes. Since control stimulation pulses can be delivered in an interleaved manner with informed pulses (e.g., when the pulses configured to contribute to therapy interfere with the detection of ECAP signals or pulse sweeps intended for posture state detection via ECAP signals do not correspond to pulses intended for therapy purposes), a clinician and/or user may select any desired electrode combination for informed pulses. Like the electrical stimulation therapy, the control stimulation may be in the form of electrical stimulation pulses or continuous waveforms. In one example, each control stimulation pulse may include a balanced, bi-phasic square pulse that employs an active recharge phase. However, in other examples, the control stimulation pulses may include a monophasic pulse followed by a passive recharge phase. In other examples, a control pulse may include an imbalanced bi-phasic portion and a passive recharge portion. Although not necessary, a bi-phasic control pulse may include an interphase interval between the positive and negative phase to promote propagation of the nerve impulse in response to the first phase of the bi-phasic pulse. The control stimulation may be delivered without interrupting the delivery of the electrical stimulation informed pulses, such as during the window between consecutive informed pulses. The control pulses may elicit an ECAP signal from the tissue, and IMD 110 may sense the ECAP signal via two or more electrodes on leads 116. In cases where the control stimulation pulses are applied to spinal cord 120, the signal may be sensed by IMD 110 from spinal cord 120.

IMD 110 can deliver control stimulation to a target stimulation site within patient 112 via the electrodes of leads 116 according to one or more ECAP test stimulation programs. The one or more ECAP test stimulation programs may be stored in a storage device of IMD 110. Each ECAP test program of the one or more ECAP test stimulation programs includes values for one or more parameters that define an aspect of the control stimulation delivered by IMD 110 according to that program, such as current or voltage amplitude, pulse width, pulse frequency, electrode combination, and, in some examples timing based on informed pulses to be delivered to patient 112. In some examples, the ECAP test stimulation program may also define the number of pules and parameter values for each pulse of multiple pulses within a pulse sweep configured to obtain a plurality of ECAP signals for respective pulses in order to obtain the growth curve that IMD 110 may use to determine the current posture state of the patient. In some examples, IMD 110 delivers control stimulation to patient 112 according to multiple ECAP test stimulation programs.

A user, such as a clinician or patient 112, may interact with a user interface of an external programmer 104 to program IMD 110. Programming of IMD 110 may refer generally to the generation and transfer of commands, programs, or other information to control the operation of IMD 110. In this manner, IMD 110 may receive the transferred commands and programs from external programmer 104 to control stimulation, such as electrical stimulation therapy (e.g., informed pulses) and/or control stimulation (e.g., control pulses). For example, external programmer 104 may transmit therapy stimulation programs, ECAP test stimulation programs, stimulation parameter adjustments, therapy stimulation program selections, ECAP test program selections, user input, or other information to control the operation of IMD 110, e.g., by wireless telemetry or wired connection.

In some cases, external programmer 104 may be characterized as a physician or clinician programmer if it is primarily intended for use by a physician or clinician. In other cases, external programmer 104 may be characterized as a patient programmer if it is primarily intended for use by a patient. A patient programmer may be generally accessible to patient 112 and, in many cases, may be a portable device that may accompany patient 112 throughout the patient's daily routine. In some examples, programmer 104 may be wearable communication devices integrated into a key fob or a wrist watch. In other examples, programmer 104 may be a handheld computing device, such as a tablet computer, computer workstation, or networked computing device. Programmer 104 may include a user interface that receives input from a user (e.g., a clinician or patient 112, respectively). The user interface may include components for interaction with a user, such as a keypad and a display. In some examples, the display may be a liquid crystal display (LCD) or light emitting diode (LED) display and the keypad may take the form of an alphanumeric keypad, or a reduced set of keys associated with particular functions. Programmer 104 can, additionally or alternatively, include a peripheral pointing device, e.g., a mouse, via which a user may interact with the user interface. In some examples, the display may include a touch screen display, and a user may interact with programmers 104 via the touch screens of the displays. In some examples, the user may also interact with programmers 104 and/or IMD 102 remotely via a networked computing device.

A patient programmer may receive input from patient 112 when the patient wishes to terminate or change electrical stimulation therapy, or when a patient perceives stimulation being delivered. In general, a physician or clinician programmer may support selection and generation of programs by a clinician for use by IMD 110, whereas a patient programmer may support adjustment and selection of such programs by a patient during ordinary use. In other examples, external programmer 104 may include, or be part of, an external charging device that recharges a power source of IMD 110. In this manner, a user may program and charge IMD 110 using one device, or multiple devices.

As described herein, information may be transmitted between external programmer 104 and IMD 110. Therefore, IMD 110 and external programmer 104 may communicate via wireless communication using any techniques known in the art. Examples of communication techniques may include, for example, radiofrequency (RF) telemetry and inductive coupling, but other techniques are also contemplated. In some examples, external programmer 104 includes a communication head that may be placed proximate to the patient's body near the IMD 110 implant site to improve the quality or security of communication between IMD 110 and external programmer 104. Communication between external programmer 104 and IMD 110 may occur during power transmission or separate from power transmission.

In some examples, IMD 110, in response to commands from external programmer 104, delivers electrical stimulation therapy according to a plurality of therapy stimulation programs to a target tissue site of the spinal cord 120 of patient 112 via electrodes (not depicted) on leads 116. In some examples, IMD 110 modifies therapy stimulation programs as therapy needs of patient 112 evolve over time. For example, the modification of the therapy stimulation programs may cause the adjustment of at least one parameter of the plurality of informed pulses. When patient 112 receives the same therapy for an extended period, the efficacy of the therapy may be reduced. In some cases, parameters of the plurality of informed pulses may be automatically updated.

In some examples, IMD 110 may detect ECAP signals from pulses delivered for the purpose of providing therapy to the patient. In other examples, the pulses configured to provide therapy to the patient may interfere with the detection of the ECAP signals. In this manner, the therapy pulses may be referred to as informed pulses because the parameter values that define the informed pulses may be determined by IMD 110 according to ECAP signals elicited from different control pulses.

In one example, each informed pulse may have a pulse width greater than approximately 300 μs, such as between approximately 300 μs and 1000 μs (i.e., 1 millisecond) in some examples. At these pulse widths, IMD 110 may not sufficiently detect an ECAP signal because the informed pulse is also detected as an artifact that obscures the ECAP signal. When pulses intended to provide therapy have these longer pulse widths, IMD 110 may deliver control stimulation in the form of control pulses in order to detect ECAP signals. The control pulses may have pulse widths of less than the interfering therapy pulses (e.g., less than approximately 300 μs), such as a bi-phasic pulse with each phase having a duration of approximately 100 μs. Since the control pulses may have shorter pulse widths than the informed pulses, the ECAP signal may be sensed and identified following each control pulse and used to inform IMD 110 about any changes that should be made to the informed pulses (and control pulses in some examples). In general, the term "pulse width" refers to the collective duration of every phase, and interphase interval when appropriate, of a single pulse. A single pulse includes a single phase in some examples (i.e., a monophasic pulse) or two or more phases in other examples (e.g., a bi-phasic pulse or a tri-phasic pulse). The pulse width defines a period of time beginning with a start time of a first phase of the pulse and concluding with an end time of a last phase of the pulse (e.g., a biphasic pulse having a positive phase lasting 100 μs, a negative phase lasting 100 μs, and an interphase interval lasting 30 μs defines a pulse width of 230 μs). In other examples, a biphasic pulse may have a positive phase lasting 120 μs, a negative phase lasting 120 μs, and an interphase interval lasting 30 μs defines a pulse width of 270 μs.

In this disclosure, efficacy of electrical stimulation therapy may be indicated by one or more characteristics of an action potential that is evoked by a stimulation pulse delivered by IMD 110 (i.e., a characteristic value of the ECAP signal). Electrical stimulation therapy delivery by leads 116 of IMD 110 may cause neurons within the target tissue to evoke a compound action potential that travels up and down the target tissue, eventually arriving at sensing electrodes of IMD 110. Furthermore, stimulation pulses (e.g., informed pulses and/or control pulses) may also elicit at least one ECAP signal, and ECAPs responsive to control stimulation may also be a surrogate for the effectiveness of the therapy and/or the intensity perceived by the patient. The amount of action potentials (e.g., number of neurons propagating action potential signals) that are evoked may be based on the various parameters of electrical stimulation pulses such as amplitude, pulse width, frequency, pulse shape (e.g., slew rate at the beginning and/or end of the pulse), etc. The slew rate may define the rate of change of the voltage and/or current amplitude of the pulse at the beginning and/or end of each pulse or each phase within the pulse. For example, a very high slew rate indicates a steep or even near vertical edge of the pulse, and a low slew rate indicates a longer ramp up (or ramp down) in the amplitude of the pulse. In some examples, these parameters contribute to an intensity of the electrical stimulation. In addition, a characteristic of the ECAP signal (e.g., an amplitude) may change based on the distance between the stimulation electrodes and the nerves subject to the electrical field produced by the delivered control stimulation pulses.

Example techniques for adjusting stimulation parameter values for informed pulses (e.g., pulses configured to contribute to therapy for the patient) are based on comparing the value of a characteristic of a measured ECAP signal to a target ECAP characteristic value for a previous control pulse. During delivery of control stimulation pulses defined by one or more ECAP test stimulation programs, IMD 110, via two or more electrodes interposed on leads 116, senses electrical potentials of tissue of the spinal cord 120 of patient 112 to measure the electrical activity of the tissue. IMD 110 senses ECAPs from the target tissue of patient 112, e.g., with electrodes on one or more leads 116 and associated sense circuitry. In some examples, IMD 110 receives a signal indicative of the ECAP from one or more sensors, e.g., one or more electrodes and circuitry, internal or external to patient 112. Such an example signal may include a signal indicating an ECAP of the tissue of patient 112. Examples of the one or more sensors include one or more sensors configured to measure a compound action potential of patient 112, or a physiological effect indicative of a compound action potential. For example, to measure a physiological effect of a compound action potential, the one or more sensors may be an accelerometer, a pressure sensor, a bending sensor, a sensor configured to detect a posture of patient 112, or a sensor configured to detect a respiratory function of patient 112. However, in other examples, external programmer 104 receives a signal indicating a compound action potential in the target tissue of patient 112 and transmits a notification to IMD 110.

In the example of FIG. 1, IMD 110 described as performing a plurality of processing and computing functions. However, external programmer 104 instead may perform one, several, or all of these functions. In this alternative example, IMD 110 functions to relay sensed signals to external programmer 104 for analysis, and external programmer 104 transmits instructions to IMD 110 to adjust the one or more parameters defining the electrical stimulation therapy based on analysis of the sensed signals. For example, IMD 110 may relay the sensed signal indicative of an ECAP to external programmer 104. External programmer 104 may compare the parameter value of the ECAP to the target ECAP characteristic value, and in response to the comparison, external programmer 104 may instruct IMD 110 to adjust one or more stimulation parameter that defines the electrical stimulation informed pulses and, in some examples, control pulses, delivered to patient 112.

In the example techniques described in this disclosure, the control stimulation parameters and the target ECAP characteristic values may be initially set at the clinic but may be set and/or adjusted at home by patient 112. For example, the target ECAP characteristics may be changed to match or be a fraction of a stimulation threshold. In some examples, target ECAP characteristics may be specific to respective different posture states of the patient. Once the target ECAP characteristic values are set, the example techniques allow for automatic adjustment of parameter values that define stimulation pulses (e.g., control pulses and/or informed pulses) to maintain consistent volume of neural activation and consistent perception of therapy for the patient when the electrode-to-neuron distance changes. The ability to change the stimulation parameter values may also allow the therapy to have long term efficacy, with the ability to keep the intensity of the stimulation (e.g., as indicated by the ECAP) consistent by comparing the measured ECAP values to the target ECAP characteristic value. In addition, or alternatively, to maintaining stimulation intensity, IMD 110 may monitor the characteristic values of the ECAP signals to limit one or more parameter values that define stimulation pulses. IMD 110 may perform these changes without intervention by a physician or patient 112.

In some examples, the system changes the target ECAP characteristic value over a period of time, such as according to a change to a stimulation threshold (e.g., a perception threshold or detection threshold). The system may be programmed to change the target ECAP characteristic in order to adjust the intensity of stimulation pulses to provide varying sensations to the patient (e.g., increase or decrease the volume of neural activation). Although the system may change the target ECAP characteristic value, received ECAP signals may still be used by the system to adjust one or more parameter values of the stimulation pulse (e.g., informed pulses and/or control pulses) in order to meet the target ECAP characteristic value.

One or more devices within system 100, such as IMD 110 and/or external programmer 104, may perform various functions as described herein. For example, IMD 110 may include stimulation circuitry configured to deliver electrical stimulation, sensing circuitry configured to sense a plurality ECAP signals, and processing circuitry. The processing circuitry may be configured to control the stimulation circuitry to deliver a plurality of electrical stimulation pulses having different amplitude values and control the sensing circuitry to detect, after delivery of each electrical stimulation pulse of the plurality of electrical stimulation pulses, a respective ECAP signal of the plurality of ECAP signals. The processing circuitry of IMD 110 may then determine, based on the plurality of ECAP signals, a posture state of the patient.

In some examples, IMD 110 may include the stimulation circuitry, the sensing circuitry, and the processing circuitry. However, in other examples, one or more additional devices may be part of the system that performs the functions described herein. For example, IMD 110 may include the stimulation circuitry and the sensing circuitry, but external programmer 104 or other external device may include the processing circuitry that at least determines the posture state of the patient. IMD 110 may transmit the sensed ECAP signals, or data representing the ECAP signal, to external programmer 104, for example. Therefore, the processes described herein may be performed by multiple devices in a distributed system. In some examples, system 100 may include one or more electrodes that deliver and/or sense electrical signals. Such electrodes may be configured to sense the ECAP signals. In some examples, the same electrodes may be configured to sense signals representative of transient movements of the patient. In other examples, other sensors, such as accelerometers, gyroscopes, or other movement sensors may be configured to sense movement of the patient that indicates the patient may have transitioned to a different posture state, by which the target characteristic value may have changed accordingly.

As described herein, the processing circuitry of IMD 110 may be configured to determine characteristic values for the plurality of ECAP signals detected after each of the plurality of electrical stimulation pulses. The characteristic value for each ECAP signal is a representation of the ECAP signal according to some metric. For example, a sensed ECAP signal may include a first peak amplitude, a second peak amplitude, and a third peak amplitude representative of propagating action potentials from the ECAP. The example duration of each peak is approximately 1 millisecond (ms). As one example, the characteristic of the ECAP may be the amplitude between the first and second peaks. This amplitude may be easily detectable even in the presence of artifacts or electronic drift in the sensed signal. In other examples, the characteristic may be an amplitude of one of the first, second, or third peaks with respect to neutral or zero voltage. In some examples, the characteristic may be a sum of two or more of the first, second, or third peaks. In other examples, the characteristic may be the area under one or more of the first, second, or third peaks. In other examples, the characteristic of the ECAP may be a ratio of one of the first, second, or third peaks to another one of the peaks. In some examples, the characteristic of the ECAP may be a slope between two points in the ECAP signal, such as a slope between two of the first, second, or third peaks. In other examples, the characteristic of the ECAP may be the time between two points of the ECAP, such as a time between two of the first, second, or third peaks. The time between when a stimulation pulse is delivered and a point in the ECAP signal may be referred to as a latency of the ECAP and may indicate the types of fibers being captured by the control stimulation pulse. The latency of the ECAP may also be a characteristic evaluated by processing circuitry 210. ECAP signals with lower latency (e.g., smaller latency values) indicate a higher percentage of nerve fibers that have faster propagation of signals, whereas ECAP signals with higher latency (e.g., larger latency values) indicate a higher percentage of nerve fibers that have slower propagation of signals. Other characteristics of the ECAP signal may be used in other examples. In this manner, each ECAP signal of the plurality of ECAP signals will be associated with a respective characteristic value of the characteristic values. As long as the distance between the electrodes and target nerve remains relatively constant during delivery of the pulses and sensing of the respective ECAP signals, higher amplitude pulses generally cause more neural recruitment and larger ECAP signals.

In one example, system 100 (which may be or include IMD 110 and/or external programmer 104) may include a stimulation generator configured to deliver a stimulation pulse to patient 112 and sensing circuitry configured to sense an ECAP signal evoked from the stimulation pulse. System 100 may also include processing circuitry configured to determine, based on the sensed values of the ECAP signal, a characteristic value of the ECAP signal, and determine, based on the characteristic value of the ECAP signal, at least one parameter value at least partially defining electrical stimulation therapy to be delivered to the patient.

One or more of the characteristic values may be used as a control signal, or feedback signal, for modulating subsequent stimulation pulses. In one example, IMD 110 may determine a difference between the characteristic value of the ECAP signal and a target ECAP characteristic value and calculate the at least one parameter value according to the difference. Processing circuitry of IMD 110 may thus be configured to control the stimulation generator to deliver the electrical stimulation therapy to the patient according to the at least one adjusted parameter value. IMD 110 may include stimulation circuitry, sensing circuitry, and processing circuitry. In some examples, other devices, such as an external device or different implanted device, may analyze ECAP signals for characteristic values and/or adjust parameter values that define stimulation pulses based on the characteristic values.

Although in one example IMD 110 takes the form of an SCS device, in other examples, IMD 110 takes the form of any combination of deep brain stimulation (DBS) devices, implantable cardioverter defibrillators (ICDs), devices to treat pelvic health conditions (including but not limited to overactive bladder (OAB) and fecal incontinence), pacemakers, cardiac resynchronization therapy devices (CRT-Ds), left ventricular assist devices (LVADs), implantable sensors, orthopedic devices, or drug pumps, as examples. Moreover, techniques of this disclosure may be used to determine stimulation thresholds (e.g., perception thresholds and detection thresholds) associated any one of the aforementioned IMDs and then use a stimulation threshold to inform the intensity (e.g., stimulation levels) of therapy.

SCS in patients has historically consisted of periodic delivery of electrical impulses to the dorsal column of the patient for the purpose of inducing paresthesia. Such electrical impulses are typically delivered at a pulse frequency less than 500 Hertz that may generally produce paresthesia for the patient. The paresthesia serves to mask pain felt in specific regions of the body, such as the lower back or legs. Sensory signals, in this case, the periodic electrical impulses from the spinal cord stimulator or the pain signal itself, are relayed to the brain via the dorsal columns of the spinal cord. The dorsal column consists of multiple sensory nerve fiber types, categorized generally by the fiber thickness and their associated signal propagation velocities. Very thick (13-20 µm) Aα fibers have action potential propagation velocities around 100 m/s and are associated with proprioception. Thick diameter (6-12 µm) Aβ fibers are heavily myelinated with action potential propagation velocities approaching 60 m/s. Paresthesia with SCS is thought to result from modulation of Aβ fibers. Thinner diameter (2-5 µm), myelinated Aδ fibers have action potential propagation velocities on the order of 10 m/s. Unmyelinated C fibers (0.2 µm-1.5 µm) transmit signals at 2 m/s. Both Aδ and C fibers are responsible for transmitting pain signals to the brain, with Aδ and C fibers contributing acute and burning pain characteristics, respectively.

There are a number of factors which may affect the propagation of signals along the spinal cord. Examples include the presence or absence of certain chemical factors, disease state, or electrical stimulation. In some instances, it is desirable to adapt a therapeutic intervention with a patient based on the measured signal propagation characteristics of the spinal cord. One method for dealing with these factors that may change over time involves detecting the ECAP signal. In various examples, an electrical stimulus is applied to the spinal cord of a patient at a particular location, and the resultant ECAP can be detected and recorded. The sensing and measurement of these ECAP signals are not limited to the spinal cord, and may also be recorded in other locations besides the spinal cord, such as peripheral nerves, or for example from within the brain.

In some examples, an IMD may adjust one or more parameters of electrical stimulation based on a detected ECAP. The ECAP may be evoked in response to the application of one or more electrical stimulation pulses that is defined according to a set of stimulation parameters. Adjustments to the electrical stimulation parameters based on the detected ECAP may provide more objective information than patient feedback. In addition, ECAP detection may allow a system to provide closed-loop stimulation control. Incorporation of ECAP into adjustment, and/or titration, of stimulation parameters may enable stimulation systems to provide stimulation therapy that uses less energy, improved patient perception of the stimulation, more targeted stimulation delivery to desired tissues, and/or improved therapeutic efficacy as compared to techniques that do not incorporate ECAP detection. In some examples, dorsal column stimulation therapy (e.g., a type of spinal cord stimulation) or other electrical stimulation therapy is provided according to a therapy program defining values for stimulation parameters, such as current or voltage amplitude, pulse frequency, pulse width, burst frequency, and/or pulse shape that are selected to provide a level of therapy, such as a reduction in, or elimination of, pain felt by the patient. Spinal cord stimulation may also include stimulation of dorsal nerve roots in some examples. Further, stimulation is not limited to stimulation of the spinal cord, and may be applied to peripheral nerves or their end organs. Further, peripheral stimulators do not have to be implanted devices, and they may also comprise non-electrical stimuli (e.g., mechanical, thermal).

In some examples, detection, or the lack thereof, of the presence of the ECAP in response to stimulation provided at a particular set of therapy parameters is used to program initial stimulation therapy parameters provided to a patient via an implantable medical device. In other examples, the detection of ECAP in response to stimulation provided at a particular set of therapy parameters may be used to automatically adjust existing stimulation therapy parameters. The presence or absence of an ECAP or a characteristic value of the ECAP in response to a set of stimulation therapy program may be used to control programming and adjustment of parameters of high frequency electrical stimulation.

For example, an IMD (or other medical device) may start providing stimulation according to an initial therapy parameter set. The IMD detects an ECAP signal that is generated by one or more nerve fibers as a result of the applied stimulation and compares a characteristic value of the ECAP signal to a target characteristic value for the ECAP. Based on the comparison, the IMD may adjust one or more parameters of the stimulation therapy so as to reduce the difference between the characteristic value of the ECAP signal and the target characteristic value for the ECAP. For example, the IMD may lower the amplitude and/or pulse frequency of the applied stimulation pulses to generate a new set of therapy parameters for subsequent therapy. The IMD may then apply the new stimulation therapy to the patient, sense the resulting ECAP generated as a result of the application of the new therapy, and may further generate a new set of therapy parameters for the therapy, in accordance with this closed loop control scheme.

In some examples, a given stimulation therapy may be applied to a patient, and the resulting ECAP signal sensed and analyzed to determine whether the patient's response to that same particular set of stimulation parameters has changed. In some examples, detection of the ECAP signal in response to a current stimulation therapy program is performed on an ongoing basis. For example, ECAP signal may be detected every few seconds, once a minute, once every few minutes, hourly, daily or weekly. In some examples, the medical device may elicit and detect an ECAP signal in response to a change in another sensed physiological parameter. For example, the medical device may pause stimulation to detect an ECAP signal when there has been a change in activity level or posture of the patient that may indicate a value of one or more parameters of the stimulation pulses should be changed (e.g., because the electrodes may have moved with respect to a target nerve). These changes in activity level and/or posture of a patient may be sensed and/or determined by a same device providing the stimulation therapy to the patient or by devices that are not the same devices providing the stimulation therapy to the patient.

In accordance with the techniques of the disclosure, system 100 senses an electrical signal via a plurality of electrodes disposed on one or more leads 116 implanted within an epidural space of patient 112 and processes the electrical signal to obtain a cardiac signal for use in controlling SCS therapy. One or more cardiac features of the cardiac signal may be indicative of pain experienced by patient 112, which in turn may be indicative of the efficacy of the SCS therapy. In one example, IMD 102 delivers, via electrodes disposed on lead 116 implanted within an epidural space of patient 112, SCS therapy to patient 112. IMD 102 senses, via the electrodes disposed on lead 116 implanted within the epidural space of the patient, an electrical signal and processes the electrical signal to extract a cardiac signal of a heart of patient 112 that comprises one or more cardiac features. Such extraction can include, but is not limited to, the isolation of actual cardiac features sensed via the recording lead 116 within the epidural space of patient 112. The one or more cardiac features may include, e.g., a heart rate of patient 112, an HRV of the heart of patient 112; an RMSSD of the heart of patient 112; a daily activity of living (DAL); or frequency domain information of the heart of patient 112. One or more cardiac features present within the cardiac signal may be indicative of pain experienced by patient 112 and may be used as a biomarker to control delivery of SCS therapy. In some examples, IMD 102 may further sense an ECAP responsive to the SCS stimulation. IMD 102 adjusts one or more parameters defining the SCS therapy based on the sensed ECAP and the one or more cardiac features within the extracted cardiac signal.

For example, IMD 102 may determine an average HRV and an average heart rate on an hourly basis, and adjust one or more electrical stimulation parameters of the SCCS therapy based on whether the average HRV and the average heart rate for the previous time period indicate whether or not a change has occurred in an amount of pain experienced by the patient. As another example, IMD 102 may use a periodically increased ECAP signal under the same stimulation amplitude without aggressor (e.g., a posture change, sneeze, or other movement) as an indication that a change has occurred in an amount of pain experienced by patient 112. When the HRV of patient 112 has decreased in comparison to a target predetermined by the clinician, IMD 102 may adjust an amplitude of the electrical stimulation therapy, as well as adjust an increase rate (INC) of the closed loop algorithm. Additionally, if IMD 102 implements therapy cycling, IMD 102 may further decrease a length of the stimulation "off" period under these circumstances in which HRV has decreased, for example. For example, IMD 102 may cycle the SCS therapy on and off based on the HRV of the heart of the patient. As another example, IMD 102 may adjust a duty cycle of the SCS therapy based on the HRV of the heart of the patient.

In some examples, IMD 102 may incorporate activity measurements of patient 112 to increase the accuracy of the detected HRV. For example, the HRV and the heart rate of patient 112 may change with different levels of activity of patient 112. IMD 102 may use sensor measurements, such as from an accelerometer, to determine an activity level of patient 112. In other examples, IMD 102 may determine one or more of an activity level, an activity state, an activity count, or a posture state of patient 112. In some examples, IMD 102 may only determine an HRV and/or a heart rate of patient 112 while IMD 102 determines that patient 112 is within a particular level of activity. For examples, IMD 102 may only determine an HRV and/or a heart rate of patient 112 while IMD 102 determines that patient 112 is active.

In another example, where IMD 102 uses therapy cycling and IMD 102 is within the stimulation "off" period, IMD 102 may actively sense, compute, and trend one or more cardiac features within the cardiac signal, such as a heart rate and HRV of patient 112. IMD 102 may combine such information with, e.g., activity intensity information for patient 112 collected via, e.g., an accelerometer of IMD 102. In response to determining that the cardiac features and activity intensity information for patient 112 are indicative of a change in an amount of pain experienced by patient 112, IMD 102 may trigger termination of the stimulation "off" period and resume delivery of SCS therapy to improve the pain condition of the patient.

In some examples, the SCS therapy is delivered as electrical stimulation therapy comprising a frequency selected from a range of 10 Hertz to 100,000 Hertz. In some examples, the SCS therapy is delivered as electrical stimulation therapy comprising a frequency selected from a range of 10 Hertz to 2,000 Hertz. In some examples, the SCS therapy is delivered as electrical stimulation therapy comprising a frequency selected from a range of 50 Hertz to 1,200 Hertz.

In some examples, the SCS therapy is delivered as electrical stimulation therapy comprising a current amplitude selected from a range of 0.1 milliamps to 20 milliamps. In some examples, the SCS therapy is delivered as electrical stimulation therapy comprising a current amplitude selected from a range of 0.5 milliamps to 20 milliamps. In some examples, the SCS therapy is delivered as electrical stimulation therapy comprising a current amplitude selected from a range of 0.5 milliamps to 15 milliamps.

In some examples, the SCS therapy is delivered as electrical stimulation therapy comprising a voltage amplitude selected from a range of 300 millivolts to 20 volts.

In some examples, IMD 102 may output, for display to a user, data related to the SCS therapy. The data for the SCS therapy may include, e.g., data related to one or more electrical stimulation therapy parameters, a sensed ECAP signal of a nerve tissue at or adjacent to target tissue site 118, or a cardiac signal determined from an electrical signal sensed from the epidural space of the patient. For example, IMD 102 may transmit, to one of external programmers 104, the data related to the SCS therapy. In some examples, one of external programmers 104 may display, via a user interface, one or more electrical stimulation therapy parameters, the sensed ECAP signal of the nerve tissue at or adjacent to target tissue site 118, or the cardiac signal determined from the electrical signal sensed from the epidural space of the patient.

In other examples, external programmers 104 transmit, via network 122, the data for the SCS therapy to remote patient monitoring system 120. Remote patient monitoring system 120 displays, via a user interface, one or more electrical stimulation therapy parameters, the sensed ECAP signal of the nerve tissue at or adjacent to target tissue site 118, or the cardiac signal determined from the electrical signal sensed from the epidural space of the patient.

FIG. 2 is a block diagram of the example IMD 102 of FIG. 1. In the example shown in FIG. 2, IMD 102 includes processing circuitry 210, memory 211, stimulation generation circuitry 202, sensing circuitry 204, switch circuitry 206, telemetry circuitry 208, sensor 212, and power source 220. Each of these circuitry blocks may be or include electrical circuitry configured to perform the functions attributed to each respective circuitry block. For example, processing circuitry 210 may include one or more processors, stimulation generation circuitry 202 may include switch circuitry, sensing circuitry 204 may include sensing circuitry, and telemetry circuitry 208 may include telemetry circuitry. Memory 211 may include any volatile or non-volatile media, such as a random access memory (RAM), read only memory (ROM), non-volatile RAM (NVRAM), electrically erasable programmable ROM (EEPROM), flash memory, and the like. Memory 211 may store computer-readable instructions that, when executed by processing circuitry 210, cause IMD 102 to perform various functions. Memory 211 may be a storage device or other non-transitory medium.

In the example shown in FIG. 2, memory 211 stores therapy programs 214 within memory 211. Each stored therapy program 214 defines one or more parameters of the electrical stimulation therapy, such as a stimulation electrode combination (i.e., active electrodes used to deliver the stimulation), electrode polarities, current or voltage amplitude, pulse width, pulse rate, and duty cycle. In some examples, the electrical stimulation parameters define a waveform for the electrical stimulation, such as rectangular or non-rectangular, rising exponentials, falling exponentials, or sinusoidal. Different waveforms may modulate the axon population differently, and may be selected so as to adjust the tissue area of patient 112 that receives electrical stimulation. In some examples, individual therapy programs may be stored as a therapy group, which defines a set of therapy programs with which stimulation may be generated.

Stimulation generation circuitry 202 generates electrical stimulation signals in accordance with the electrical stimulation parameters noted above. Other ranges of therapy parameter values may also be useful, and may depend on the target stimulation site within patient 112. While stimulation pulses are described, stimulation signals may be of any form, such as continuous-time signals (e.g., sine waves) or the like.

Switch circuitry 206 may include one or more switch arrays, one or more multiplexers, one or more switches (e.g., a switch matrix or other collection of switches), or other electrical circuitry configured to direct stimulation signals from stimulation generation circuitry 202 to one or more of electrodes 114, 116, or directed sensed signals from one or more of electrodes 114, 116 to sensing circuitry 204. In other examples, stimulation generation circuitry 202 and/or sensing circuitry 204 may include sensing circuitry to direct signals to and/or from one or more of electrodes 114, 116, which may or may not also include switch circuitry 206.

Processing circuitry 210 may include any one or more of a microprocessor, a controller, a digital signal processor (DSP), an application specific integrated circuit (ASIC), a field-programmable gate array (FPGA), discrete logic circuitry, or any other processing circuitry configured to provide the functions attributed to processing circuitry 210 herein may be embodied as firmware, hardware, software or any combination thereof. Processing circuitry 210 controls stimulation generation circuitry 202 according to therapy programs 214 stored in memory 211 to apply particular stimulation parameter values specified by one or more of programs, such as amplitude, pulse width, pulse rate, and duty cycle.

In the example of FIG. 2, IMD 102 comprises two leads 116 comprising sets of electrodes 114, 115. In some examples, leads 116 comprise percutaneous SCS leads configured to be implanted within an epidural space of patient 112 of FIG. 1. The epidural space may include, e.g., a thoracic region or a lumbar region of patient 112. In the example shown in FIG. 2, the set of electrodes 114 includes electrodes 114A, 114B, 114C, 114D, 114D, 114F, 114G, and 114H and the set of electrodes 115 includes electrodes 115A, 115B, 115C, 115D, 115E, 115F, 115G, and 115H. While in the example of FIG. 2, each lead 116 comprises 8 electrodes 114 or 115, in other examples, each lead 116 may have fewer or more electrodes. For example, each lead 116 may include only 4 electrodes, only 2 electrodes, or a single electrode. Processing circuitry 210 also controls stimulation generation circuitry 202 to generate and apply the stimulation signals to selected combinations of electrodes 114, 115. In some examples, stimulation generation circuitry 202 includes switch circuitry that couples stimulation signals to selected conductors within leads 16, which, in turn, deliver the stimulation signals across selected electrodes 114, 115. Such switch circuitry may be a switch array, switch matrix, multiplexer, or any other type of switching circuitry configured to selectively couple stimulation energy to selected electrodes 114, 115 and to selectively sense bioelectrical neural signals of spine 20 with selected electrodes 114, 115.

In other examples, however, stimulation generation circuitry 202 comprises a plurality of pairs of voltage sources, current sources, voltage sinks, or current sinks connected to each of electrodes 114, 115 such that each pair of electrodes has a unique signal generator. In other words, in these examples, each of electrodes 114, 115 is independently controlled via its own signal generator (e.g., via a combination of a regulated voltage source and sink or regulated current source and sink), as opposed to switching signals between electrodes 114, 115.

Stimulation generation circuitry 202 may be a single channel or multi-channel stimulation generator. In particular, stimulation generation circuitry 202 may be capable of delivering a single stimulation pulse or multiple stimulation pulses at a given time via a single electrode combination or multiple stimulation pulses at a given time via multiple electrode combinations. In some examples, however, stimulation generation circuitry 202 may be configured to deliver multiple channels on a time-interleaved basis. For example, switch circuitry of stimulation generation circuitry 202 may serve to time divide the output of stimulation generation circuitry 202 across different electrode combinations at different times to deliver multiple programs or channels of stimulation energy to patient 112.

In another example, the stimulation generation circuitry 202 may control the independent sources or sinks on a time-interleaved basis. In some examples, stimulation generation circuitry 202 cycles through different stimulation parameters in blocks. In other examples, stimulation generation circuitry 202 interleaves different stimulation parameters with one another to create a composite electrical stimulation program. In yet further examples, stimulation generation circuitry 202 cycles between periods of time where electrical stimulation is delivered and periods of time in which no electrical stimulation is delivered. In such examples, processor 210 may control stimulation generation circuitry 202 to vary the length of a duty cycle of the period (e.g., the ratio of time where electrical stimulation is delivered versus the total length of the period). In some examples, stimulation generation circuitry 202 includes circuitry configured to provide active or passive charge balancing so as to balancing electrical charge induced by delivery of the electrical stimulation.

In some examples, stimulation generation circuitry 202 includes a switch circuit (instead of, or in addition to, switch circuitry 206) that may couple stimulation signals to selected conductors within leads 116, which, in turn, deliver the stimulation signals across selected electrodes 114, 115. Such a switch circuit may be a switch array, switch matrix, multiplexer, or any other type of switching circuit configured to selectively couple stimulation energy to selected electrodes 114, 115 and to selectively sense bioelectrical neural signals of a spinal cord of the patient (not shown in FIG. 2) with selected electrodes 114, 115.

Electrodes 114, 115 on respective leads 16 may be constructed of a variety of different designs. For example, one or both of leads 16 may include two or more electrodes at each longitudinal location along the length of the lead, such as multiple electrodes at different perimeter locations around the perimeter of the lead at each of the locations A, B, C, and D. In one example, the electrodes may be electrically coupled to stimulation generation circuitry 202 via respective wires that are straight or coiled within the housing the lead and run to a connector at the proximal end of the lead. In another example, each of the electrodes of the lead may be electrodes deposited on a thin film. The thin film may include an electrically conductive trace for each electrode that runs the length of the thin film to a proximal end connector. The thin film may then be wrapped (e.g., a helical wrap) around an internal member to form the lead 16. These and other constructions may be used to create a lead with a complex electrode geometry.

Although sensing circuitry 204 is incorporated into a common housing with stimulation generation circuitry 202 and processing circuitry 210 in FIG. 2, in other examples, sensing circuitry 204 may be in a separate housing from IMD 102 and may communicate with processing circuitry 210 via wired or wireless communication techniques. Example electrical signals include, but are not limited to, a signal generated from local field potentials within one or more regions of spine 20.

Sensor 212 may include one or more sensing elements that sense values of a respective patient parameter. For example, sensor 212 may include one or more accelerometers, optical sensors, chemical sensors, temperature sensors, pressure sensors, or any other types of sensors. Sensor 212 may output patient parameter values that may be used as feedback to control delivery of therapy. IMD 102 may include additional sensors within the housing of IMD 102 and/or coupled via one of leads 16 or other leads. In addition, IMD 102 may receive sensor signals wirelessly from remote sensors via telemetry circuitry 208, for example. In some examples, one or more of these remote sensors may be external to patient (e.g., carried on the external surface of the skin, attached to clothing, or otherwise positioned external to the patient).

Telemetry circuitry 208 supports wireless communication between IMD 102 and an external programmer 104 or another computing device under the control of processing circuitry 210. Processing circuitry 210 of IMD 102 may receive, as updates to programs, values for various stimulation parameters such as amplitude and electrode combination, from programmer 104 via telemetry circuitry 208. The updates to the therapy programs may be stored within therapy programs 214 portion of memory 211. Telemetry circuitry 208 in IMD 102, as well as telemetry circuitry in other devices and systems described herein, such as programmer 104, may accomplish communication by radiofrequency (RF) communication techniques. In addition, telemetry circuitry 208 may communicate with external medical device programmer 104 via proximal inductive interaction of IMD 102 with programmer 104. Accordingly, telemetry circuitry 208 may send information to external programmer 104 on a continuous basis, at periodic intervals, or upon request from IMD 102 or programmer 104.

Power source 220 delivers operating power to various components of IMD 102. Power source 220 may include a small rechargeable or non-rechargeable battery and a power generation circuit to produce the operating power. Recharging may be accomplished through proximal inductive interaction between an external charger and an inductive charging coil within IMD 220. In some examples, power requirements may be small enough to allow IMD 220 to utilize patient motion and implement a kinetic energy-scavenging device to trickle charge a rechargeable battery. In other examples, traditional batteries may be used for a limited period of time.

Telemetry circuitry 208 of IMD 102 receives commands from an external programmer 104. In response to these commands, processing circuitry 210 of IMD 102 controls stimulation generation circuitry 202 to deliver electrical stimulation therapy programs to a target tissue area of the spinal column 20 of patient 112 via electrodes 114, 115 of leads 16.

In some examples, processing circuitry 210 receives, via sensing circuitry 204, a sensed ECAP. Based on the sensed ECAP, processing circuitry 210 determines an appropriate adjustment to one or more current stimulation therapy parameters in order to achieve a target ECAP characteristic value. In some examples, a current characteristic value of the ECAP signal may be compared to a target ECAP characteristic value (e.g., a numerical value for a characteristic or an ECAP signal template) corresponding to efficacious therapy.

Processing circuitry 210 analyzes the sensed ECAP signal to determine values of different types of characteristics. For example, a sensed ECAP signal may include a first peak amplitude, a second peak amplitude, and a third peak amplitude representative of propagating action potentials from the ECAP. The example duration of each peak is approximately 1 millisecond (ms). As one example, the characteristic of the ECAP may be the amplitude between the first and second peaks. This amplitude may be easily detectable even in the presence of artifacts or electronic drift in the sensed signal. In other examples, the characteristic may be an amplitude of one of the first, second, or third peaks with respect to neutral or zero voltage. In some examples, the characteristic may be a sum of two or more of the first, second, or third peaks. In other examples, the characteristic may be the area under one or more of the first, second, or third peaks. In other examples, the characteristic of the ECAP may be a ratio of one of the first, second, or third peaks to another one of the peaks. In some examples, the characteristic of the ECAP may be a slope between two points in the ECAP signal, such as a slope between two of the first, second, or third peaks. In other examples, the characteristic of the ECAP may be the time between two points of the ECAP, such as a time between two of the first, second, or third peaks. The time between when a stimulation pulse is delivered and a point in the ECAP signal may be referred to as a latency of the ECAP and may indicate the types of fibers being captured by the control stimulation pulse. The latency of the ECAP may also be a characteristic evaluated by processing circuitry 210. ECAP signals with lower latency (e.g., smaller latency values) indicate a higher percentage of nerve fibers that have faster propagation of signals, whereas ECAP signals with higher latency (e.g., larger latency values) indicate a higher percentage of nerve fibers that have slower propagation of signals. Other characteristics of the ECAP signal may be used in other examples.

The amplitude of the ECAP signal increases with increased amplitude of the stimulation pulse, as long as the pulse amplitude is greater than a threshold such that nerves depolarize and propagate the signal. A target ECAP characteristic (e.g., a target ECAP amplitude) may be determined from the ECAP signal detected from a stimulation pulse to deliver effective therapy to the patient. The ECAP signal thus is representative of the distance between the stimulation electrodes and the nerves appropriate for the stimulation parameter values of the stimulation pulses delivered at that time. Therefore, processing circuitry 210 may attempt to use detected changes to the measured ECAP characteristic value to change stimulation pulse parameter values and maintain the target ECAP characteristic value during delivery of the primary stimulation pulses and master stimulation pulse.

Therefore, IMD 102 may be configured to provide ECAP responsive stimulation therapy to patient 112. Stimulation adjustments in response to changes in ECAP signals or to patient state may be automatic or semi-automatic (subject to patient approval). In many cases, fully automatic adjustments may be desirable so that IMD 102 may react more quickly to changes in patient state, or changes in therapy efficacy that may be unrelated to a change in patient state. In some examples, ECAP sensing and analysis may be used to refine stimulation therapy programs selected based on sensed posture.

According to the techniques of this disclosure, processing circuitry 210 controls stimulation generation circuitry 202 to deliver SCS therapy to patient 112. For example, processing circuitry 210 may control stimulation generation circuitry 202 to deliver SCS therapy by delivering electrical stimulation therapy via one or more electrodes 114, 115 disposed on lead 116 to target spinal cord 120 of FIG. 1, which is located within an epidural space of patient 112.

Sensing circuitry 204 senses, via one or more electrodes 114, 115 disposed on leads 116, an electrical signal. Sensing circuitry 204 may apply one or more filters to the electrical signal to extract various signals present within the electrical signal. For example, sensing circuitry 204 obtains from the electrical signal an ECAP response to the SCS stimulation. In some examples, the ECAP response is an ECAP response of a nerve tissue located at or adjacent to spinal cord 120 within the epidural space of patient 112. As a further example, sensing circuitry 204 applies a low pass filter to the electrical signal to obtain a cardiac signal comprising one or more cardiac features.

Processing circuitry 210 adjusts one or more electrical stimulation therapy parameters defining the SCS therapy based on the sensed ECAP response and the one or more cardiac features of the cardiac signal. For example, processing circuitry 210 determines an appropriate adjustment to one or more electrical stimulation therapy parameters in order to achieve both a target ECAP characteristic value and a target value of the one or more cardiac features of the cardiac signal. In some examples, a characteristic value of the ECAP signal may be compared to a target ECAP characteristic value (e.g., a numerical value for a characteristic or an ECAP signal template) corresponding to efficacious therapy.

As another example, processing circuitry 210 determines whether the cardiac features are indicative of increased pain in patient 112. For example, HRV may generally decline as a symptom of poor health status, and hence heart rate (HR) becomes elevated. Improved HRV is associated with improved physical functioning. Decreased HRV is common among fibromyalgia patients. Additionally, fibromyalgia can be treated with SCS. Therefore, a decreasing HRV of patient 112 may be indicative that patient 112 is experiencing increased pain. In response, processing circuitry 210 may increase a value of one or more electrical stimulation therapy parameters defining the SCS therapy so as to increase the efficacy of the SCS therapy provided to patient 112.

As another example, processing circuitry 210 determines whether the cardiac features are indicative of decreased pain in patient 112. For example, an increasing HRV of patient 112 may be indicative that patient 112 is experiencing decreased pain. In response, processing circuitry 210 may decrease a value of one or more electrical stimulation therapy parameters defining the SCS therapy so as to decrease the power consumption of IMD 102 and thereby increase the battery longevity of IMD 102 where relatively stronger, and more power consuming, therapy programs are not needed to provide efficacious therapy to patient 112.

SCS therapy generally has a wash-in period (or induction period) after a patient is implanted with an IMD such as IMD 102. The wash-in period is a period of time during which the body of patient 112 adapts to the SCS therapy and during which the efficacy of the SCS therapy to patient 112 may substantially change. Therefore, it may be desired not to adjust any therapy parameters of the SCS therapy for a certain period of time after implantation of the IMD. Furthermore, this wash-in period may vary or be different from patient to patient. In some examples, IMD 102 may use the detected cardiac features, such as HRV, together with other sensed signals, such as accelerometer signals, to estimate the length of the wash-in or induction period. After IMD 102 determines that the wash-in period has concluded, IMD 102 may enable the adjustment of therapy (e.g., by adjusting one or more parameters defining the SCS therapy or by cycling times during which IMD 102 delivers therapy (e.g., "ON" times) and times during which IMD 102 does not deliver therapy (e.g., "OFF" times) to optimize therapy. For example, IMD 102 may decrease an amplitude of the SCS therapy and/or increase an OFF time which IMD 102 does not deliver therapy so as to reduce a power consumption of the SCS therapy.

Therefore, as described above, processing circuitry 210 may use both a target ECAP characteristic value and a target value of the one or more cardiac features of the cardiac signal to control adjustment of one or more electrical stimulation therapy parameters defining the SCS therapy. By using the one or more cardiac features of the cardiac signal to control the adjustment of the one or more electrical stimulation therapy parameters, an 1 MB as described herein may provide increased efficacy of SCS therapy to patient 112 over a system that controls therapy using an ECAP characteristic value alone.

FIG. 3 is a block diagram of an example external programmer 104 of FIG. 1. Although programmer 104 may generally be described as a hand-held device, programmer 104 may be a larger portable device or a more stationary device. In addition, in other examples, programmer 104 may be included as part of an external charging device or include the functionality of an external charging device. As illustrated in FIG. 3, programmer 104 may include processing circuitry 310, memory 311, user interface 302, telemetry circuitry 308, and power source 320. Memory 311 may store instructions that, when executed by processing circuitry 310, cause processing circuitry 310 and external programmer 104 to provide the functionality ascribed to external programmer 104 throughout this disclosure. Each of these components, or circuitry, may include electrical circuitry that is configured to perform some or all of the functionality described herein. For example, processing circuitry 310 may include one or more processors configured to perform the operations discussed above with respect to processing circuitry 310.

In general, programmer 104 comprises any suitable arrangement of hardware, alone or in combination with software and/or firmware, to perform the techniques attributed to programmer 104, and processing circuitry 310, user interface 302, and telemetry circuitry 308 of programmer 104. In various examples, programmer 104 may include one or more processors, such as one or more microprocessors, DSPs, ASICs, FPGAs, or any other equivalent integrated or discrete logic circuitry, as well as any combinations of such components. Programmer 104 also, in various examples, may include a memory 311, such as RAM, ROM, PROM, EPROM, EEPROM, flash memory, a hard disk, a CD-ROM, comprising executable instructions for causing the one or more processors to perform the actions attributed to them. Moreover, although processing circuitry 310 and telemetry circuitry 308 are described as separate circuits, in some examples, processing circuitry 310 and telemetry circuitry 308 are functionally integrated. In some examples, processing circuitry 310 and telemetry circuitry 308 correspond to individual hardware units, such as ASICs, DSPs, FPGAs, or other hardware units.

Memory 311 (e.g., a storage device) may store instructions that, when executed by processing circuitry 310, cause processing circuitry 310 and programmer 104 to provide the functionality ascribed to programmer 104 throughout this disclosure. For example, memory 311 may include instructions that cause processing circuitry 310 to obtain one or more parameters from memory, or receive a user input and send a corresponding command to IMD 104, or instructions for any other functionality. In addition, memory 311 may include a plurality of therapy programs 214, where each program includes one or more parameters that defines stimulation therapy.

User interface 302 may include a button or keypad, lights, a speaker for voice commands, a display, such as a liquid crystal (LCD), light-emitting diode (LED), or organic light-emitting diode (OLED). In some examples the display may be a touch screen. User interface 302 may be configured to display any information related to the delivery of stimulation therapy, identified patient behaviors, sensed patient parameter values, patient behavior criteria, or any other such information. User interface 302 may also receive user input via user interface 302. The input may be, for example, in the form of pressing a button on a keypad or selecting an icon from a touch screen. The input may request starting or stopping electrical stimulation, or the input may request some other change to the delivery of electrical stimulation.

Telemetry circuitry 308 may support wireless communication between IMD 102 and programmer 104 under the control of processing circuitry 310. Telemetry circuitry 308 may also be configured to communicate with another computing device via wireless communication techniques, or direct communication through a wired connection. In some examples, telemetry circuitry 308 provides wireless communication via an RF or proximal inductive medium. In some examples, telemetry circuitry 308 includes an antenna, which may take on a variety of forms, such as an internal or external antenna.

Examples of local wireless communication techniques that may be employed to facilitate communication between programmer 104 and IMD 102 include RF communication according to the 802.11 or Bluetooth specification sets or other standard or proprietary telemetry protocols. In this manner, other external devices may be capable of communicating with programmer 104 without needing to establish a secure wireless connection. As described herein, telemetry circuitry 308 may be configured to transmit a spatial electrode movement pattern or other stimulation parameter values to IMD 102 for delivery of stimulation therapy.

In some examples, selection of therapy parameters or therapy programs may be transmitted to a medical device (e.g., IMD 102) for delivery to patient 112. In other examples, the therapy may include medication, activities, or other instructions that patient 112 must perform themselves or a caregiver perform for patient 112. In some examples, programmer 104 may provide visual, audible, and/or tactile notifications that indicate there are new instructions. Programmer 104 may require receiving user input acknowledging that the instructions have been completed in some examples.

In accordance with the techniques of the disclosure, user interface 302 is configured to display data related to SCS therapy delivered by IMD 102 of FIG. 1. In some examples, processing circuitry 310 receives, via telemetry circuitry 308 and from IMD 102, data related to SCS therapy delivered by IMD 102. User interface 302 may display the data related to SCS therapy delivered by IMD 102. For example, user interface 302 may display one or more electrical signals sensed by IMD 102, an ECAP response of a nerve tissue located at or adjacent to spinal cord 120 within the epidural space of patient 112, a cardiac signal (and/or one or more cardiac features) of a heart of patient 112 that is determined from the electrical signal sensed from the epidural space of patient 112, or one or more electrical stimulation parameters defining the SCS therapy delivered by IMD 102.

In some examples, user interface 302 further displays an accelerometer signal, which may correspond to an activity level of patient 112. In some examples, user interface 302 may group different values of an accelerometer signal into activity states, such as rest, minimally active, moderately active, highly active or very highly active. In some examples, these activity states are derived from activity states of a general population. In some examples, these activity states are individualized for each patient 112.

FIG. 4 is a graph illustrating example signals 400, 402, 404 sensed in accordance with the techniques of the disclosure. In some examples, IMD 102 delivers, via one or more electrodes disposed on lead 116, SCS therapy to spinal cord 120, which is located within an epidural space of patient 112. IMD 102 may also sense, via one or more electrodes disposed on lead 116, electrical signal 400. In the example of FIG. 4, electrical signal 400 is a raw signal collected from SCS lead 116 without signal filtering and while IMD 102 delivers the SCS therapy. Signal 402 is an electrocardiogram (ECG) sensed via one or more electrodes external to patient 112. IMD 102 may apply signal processing, such as filtering, to obtain filtered signal 404.

In some examples, IMD 102 may sense, via each pair of a plurality of pairs of electrodes 114, 115, a cardiac signal. IMD 102 analyzes each cardiac signal sensed via each pair of the plurality of pairs of electrodes 114, 115 to select a pair of electrodes 114, 115 that has a desired signal-to-noise (SNR) ratio. For example, IMD 102 selects a pair of electrodes 114, 115 that has an SNR greater than a predetermined threshold. As another example, IMD 102 selects a pair of electrodes 114, 115 that has an SNR greater than an SNR of each other pair of electrodes 114, 115. In some examples, the selected pair of electrodes 114, 115 is different from a pair of electrodes 114, 115 that are used to sense one or more ECAPs. IMD 102 uses cardiac signal sensed from the selected pair of electrodes 114, 115 to obtain filtered signal 404 for use in obtaining the one or more cardiac features as described below.

In the example of FIG. 4, filtered signal 404 depicts a cardiac signal comprising one or more cardiac features of patient 112, such as one or more P complexes 405 or one or more QRS complexes 406. Furthermore, the one or more cardiac features may include one or more measurements derived from the cardiac signal, such as a width of P complex 405, a width of QRS complex 406, a PR interval, a PP period, a P-QRS period, a QRS-QRS period, a QRS interval, or a QT interval, a QT duration, etc. In some examples, the one or more cardiac features may include a heart rate of patient 112, such as a daytime or nighttime heart rate of patient 112.

FIG. 5 is a graph illustrating example signals 500, 502 sensed in accordance with the techniques of the disclosure. In some examples, IMD 102 delivers, via one or more electrodes disposed on lead 116, SCS therapy to spinal cord 120, which is located within an epidural space of patient 112 and senses, via one or more electrodes disposed on lead 116, electrical signal 500. In the example of FIG. 5, electrical signal 500 is a raw signal collected from SCS lead 116 without signal filtering and while IMD 102 delivers the SCS therapy. IMD 102 may apply signal processing, such as filtering, to obtain filtered signal 502. In some examples, IMD 102 applies a low-pass filter with a cutoff frequency of about 25 Hertz. In the example of FIG. 5, filtered signal 502 is a filtered signal from which IMD 102 has removed artifacts resulting from electrical stimulation by IMD 102, ECAP responses from nerve tissue located at or adjacent to spinal cord 120, as well as other noise or signal artifacts. Filtered signal 502 results in a cardiac signal of a heart of patient 112 that is sensed from the epidural space of patient 112. Filtered signal 502 may exhibit one or more cardiac features 506 of the heart of patient 112. In some examples, IMD 102 gates delivery of SCS stimulation to a cardiac cycle of the heart of patient 112 such that IMD 102 may delivery SCS stimulation at a particular point in the cardiac cycle or avoid delivery of SCS stimulation during a particular phase of the cardiac cycle (e.g., so as to avoid introducing artifacts into sensed cardiac features 506.

FIG. 6 is an illustration of an example user interface in accordance with the techniques of the disclosure. In some examples, user interface 600 is an example of user interface 302 of external programmer 104 of FIG. 3. User interface 600 may be used to adjust one or more therapy parameters of one or more electrodes 114, 115 of leads 116 of IMD 102 of FIGS. 1 and 2. FIG. 6 depicts display window 602 of user interface 600, which is displaying example lead icons 616. In some examples, user interface 600 may display a single lead icon or a plurality of lead icons representing respective leads, each lead having one or more electrodes 114, 115.

In the example of FIG. 6, window 602 graphically depicts example lead icons 616 that may correspond to one of leads 116 in FIG. 1. In the illustrative example, lead icons 616 include multiple electrode icons, namely electrode icons 614A-614D and 615A-615D (referred to collectively as "electrode icons 614, 615"). Lead icons 616 may have more, or fewer, electrode icons 614, 615, depending on the particular lead configuration in use. For ease of illustration, only four electrode icons 614, 615 (or a portion of four electrodes) are depicted on each lead icon 616. In addition, window 602 may depict stimulation zones, electrical field zones, activation zones, etc. (not shown). For example, a zone may be an anodal zone generated by one or more of electrodes 114, 115 of leads 116 sourcing current. A second zone may be a cathodal zone generated by one or more of electrodes 114, 115 of leads 116 sinking current.

In the example of FIG. 6, adjacent to each of the four electrodes, display window 602 may indicate one or more electrical stimulation therapy parameters for SCS therapy associated with each of electrodes 114, 116 or each electrode combination. In particular, user interface 602 may depict one or more fillable or otherwise adjustable fields. Each field may indicate a value of a therapy parameter of each of electrodes 114, 116, such as, for example, example current amplitude field 606, example cycle duration field 608, or example duty cycle field 610 of FIG. 6. In other examples, such fields may permit a user to adjust other electrical stimulation therapy parameters not expressly depicted in FIG. 6, such as one of a voltage amplitude or a current amplitude, an electrical stimulation pulse width, an electrical stimulation pulse count, a duty cycle of the electrical stimulation, an electrical stimulation pulse rate or a frequency of the electrical stimulation, etc. Fields 606, 608, 610 may apply equally to all electrodes, including segmented electrodes in the case of a segmented lead implementation, or may be specific to a single electrode, such as an electrode corresponding to a selected electrode icon 614, 615.

In accordance with the techniques of the disclosure, user interface 600 further includes display window 604. Display window 604 depicts a graph of one or more electrical signals sensed by IMD 102. For example, display window 604 depicts, e.g., one or more of signals 400, 402, 404 of the graph depicted in FIG. 4 or one or more of signals 500, 502 of the graph depicted in FIG. 5. In some examples, display window 604 depicts a graph of a cardiac signal of a heart of patient 112 that is sensed from the epidural space of patient 112. In some examples, IMD 102 removes artifacts from the electrical signal resulting from electrical stimulation by IMD 102, ECAP responses from nerve tissue located at or adjacent to spinal cord 120, as well as other noise or signal artifacts to obtain the cardiac signal. The cardiac signal may comprise one or more cardiac features. In some examples, display window 604 depicts one or more of a combination of an electrical signal sensed from the epidural space of patient 112, an ECAP response extracted from the electrical signal, or a cardiac signal extracted from the electrical signal. Typically, IMD 102 may record the electrical signal sensed from the epidural space of patient 112, the ECAP response extracted from the electrical signal, and a cardiac signal extracted from the electrical signal over a period of time such that display window 604 may display the electrical signal sensed from the epidural space of patient 112, the ECAP response extracted from the electrical signal, and a cardiac signal extracted from the electrical signal, or changes therein, over the period of time. Further, display window 604 may display, over the period of time, other patient data, such as heart rate, HRV, one or more stimulation parameters, ECAP values, etc. to enable a clinician to view how the sensed data corresponds to the delivery of SCS stimulation. In some examples, display window 604 may depict one or more aspects of patient data as a graph or chart along a time axis corresponding to seconds, minutes, days, months, etc. In this fashion, display window 604 may enable a clinician to understand how such data correlates to changes in pain experienced by the patient, as well as how such changes in pain experienced by the patient may correlate to delivery of SCS stimulation. The clinician may use such information to adjust one or more parameters of the SCS stimulation so as to increase the efficacy of SCS stimulation delivered to the patient.

FIGS. 7A-7B are flowcharts illustrating an example operation in accordance with the techniques of the disclosure. The operation of FIGS. 7A-7B may be performed, e.g., by IMD 102 of FIG. 1 and may operate in conjunction with one another or independently from one another. As depicted in the example of FIG. 7A, IMD 102 delivers electrical stimulation therapy via one or more electrodes disposed on lead 116 to spinal cord 120, which is located within an epidural space of patient 112 (702). IMD 102 senses, via one or more electrodes disposed on lead 116, an electrical signal and processes the electrical signal to obtain an ECAP signal responsive to the electrical stimulation and a cardiac signal of patient 112. IMD 102 may further process the cardiac signal to identify one or more cardiac features indicative of activity of a heart of patient 112 (704).

IMD 102 determines whether the cardiac features are indicative of a change in pain experienced by patient 112, e.g., whether the cardiac features are trending towards increased pain (706). For example, a decreasing HRV of patient 112 may be indicative that patient 112 is experiencing increased pain. In response to determining that the cardiac features are not trending towards increased pain (e.g., "NO" block of 706), the operation returns to sensing block 704 and IMD 102 continues to sense the electrical signal and extract ECAP signals and cardiac signals of patient 112.

In response to determining that the cardiac features are trending towards increased pain (e.g., "YES" block of 706), IMD 102 determines whether the sensed ECAP signal is within a targeted ECAP signal range (708). In response to determining that the sensed ECAP signal is not within the targeted ECAP signal range (e.g., "NO" block of 708), IMD 102 adjusts one or more stimulation parameters defining the electrical stimulation therapy (710). The operation returns to 702 and IMD 102 delivers electrical stimulation therapy to spinal cord 120 according to the adjusted stimulation parameters.

In the foregoing example of FIG. 7A, IMD 102 uses a sensed ECAP signal to adjust stimulation parameters. However, in other examples not depicted herein, IMD 102 may not sense ECAP signals at all. In such a configuration, IMD 102 may adjust the stimulation parameters based on the change in pain experienced by the patient without informing the adjustment of stimulation parameters via sensed ECAP signals.

In response to determining that the sensed ECAP signal is within the targeted ECAP signal range (e.g., "YES" block of 708), IMD 102 determines whether the current stimulation amplitude is below a targeted maximum stimulation amplitude (712). The targeted maximum stimulation amplitude may be, e.g., set for an ECAP-based closed loop. In response to determining that the current stimulation amplitude is below the targeted maximum stimulation amplitude (e.g., "YES" block of 712), IMD 102 increases the stimulation amplitude (716). For example, IMD 102 may increase one of a current amplitude or a voltage amplitude defining the electrical stimulation therapy. The operation returns to 702 and IMD 102 delivers electrical stimulation therapy to spinal cord 120 according to the adjusted stimulation parameters.

In response to determining that the current stimulation amplitude is not below the targeted maximum stimulation amplitude (e.g., "NO" block of 712), IMD 102 may change to an alternative therapy parameter set that defines one or more alternative backup therapy pulses (714). The operation returns to 702 and IMD 102 delivers electrical stimulation therapy to target spinal cord 120 according to the alternative backup therapy pulses. In some examples, an alternative backup therapy comprises a different pattern of electrical stimulation using the same combination of electrodes as the initial therapy. In some examples, the alternative backup therapy comprises a different pattern of electrical stimulation using a different combination of electrodes than the initial therapy, e.g., by using different pairs of electrodes to maintain a requirement for maintaining physical separation between stimulation and sensing electrodes. In some examples, the alternative backup therapy comprises one or more adjustments to one or more parameters of the initial therapy. For example, the alternative backup therapy may comprise one or more of an increase in a current or a voltage amplitude, an increase in a frequency, or an increase in a pulse duration.

FIG. 7B illustrates an example closed-loop policy for cycling stimulation on and off based on the pain biomarker determined from one or more cardiac features. As depicted in the example of FIG. 7B, IMD 102 operates in a monitoring mode (752). While in the monitoring mode, IMD 102 delivers no electrical stimulation therapy to patient 112. Further, IMD 102 may sense electrical signals and/or record patient data for telemetric medicine or remote healthcare purposes. IMD 102 determines whether one or more cardiac features extracted from the cardiac signal are indicative of a change in pain experienced by patient 112, e.g., whether the cardiac features are trending towards increased pain in patient 112 (754). For example, a decreasing HRV of patient 112 may be indicative that patient 112 is experiencing increased pain. In response to determining that the cardiac features are not trending towards increased pain (e.g., "NO" block of 754), IMD 102 determines whether a predetermined stimulation activation time has occurred (756). In response to determining that the predetermined stimulation activation time has not occurred (e.g., "NO" block of 756), the operation returns to block 754 and IMD determines whether subsequently sensed cardiac features are trending toward increased pain.

In response to determining that the cardiac features are trending towards increased pain (e.g., "YES" block of 754), or in response to determining that the predetermined stimulation activation time has occurred (e.g., "YES" block of 756), IMD 102 delivers electrical stimulation therapy via one or more electrodes disposed on lead 116 to spinal cord 120, which is located within an epidural space of patient 112 (758). In this manner, IMD 102 can automatically trigger stimulation deliver in response to determining that one or more cardiac features have exceeded a respective or collective threshold indicating increased pain. In other examples, IMD 102 can turn off, or disable, stimulation delivery in response to determining that one or more cardiac features are below a respective or collective threshold indicating decreased pain and stimulation is no longer required. Alternatively, instead of cycling stimulation on and off, IMD 102 may perform a process similar as discussed with FIG. 7B by increasing or decreasing stimulation intensity (e.g., one or more of an amplitude, pulse width, or frequency value) in response to detecting an increase or decreasing in cardiac feature values, respectively.

In some examples, IMD 102 may only sense cardiac features of patient 112 when patient 112 is in known state, such as sleeping, lying down, etc. For example, IMD 102 may initially determine a state of that patient, such as a sleep state, an activity level, an activity state, or a posture state of patient 112. In response to determining that the patient is in a particular state (e.g., "sleeping," "prone," etc.) IMD 102 senses the electrical signal from patient 112 and processes the electrical signal to obtain the one or more cardiac features. IMD 102 further determines a pain metric for patient 112 from the one or more cardiac features and controls delivery of the SCS therapy based on the pain metric for patient 112.

FIG. 8 is a flowchart illustrating an example operation in accordance with the techniques of the disclosure. The operation of FIG. 8 may be performed, e.g., by IMD 102 of FIG. 1. As depicted in the example of FIG. 8, IMD 102 delivers SCS therapy to patient 112 (802). For example, IMD 102 may deliver SCS therapy by delivering electrical stimulation therapy via one or more electrodes disposed on lead 116 to spinal cord 120, which is located within an epidural space of patient 112.

IMD 102 senses, via the one or more electrodes disposed on lead 116, an electrical signal (804). IMD 102 may apply one or more filters to the electrical signal to extract various signals present within the electrical signal. For example, IMD 102 obtains an ECAP response from the electrical signal responsive to the SCS stimulation (806). In some examples, the ECAP response is an ECAP response of a nerve tissue located at or adjacent to spinal cord 120 within the epidural space of patient 112. As a further example, IMD 102 applies a low pass filter (e.g., a filter with a cut-off at approximately 25 Hz) to the electrical signal to obtain a cardiac signal comprising one or more cardiac features of the heart of patient 112 (808).

IMD 102 adjusts one or more electrical stimulation therapy parameters defining the SCS therapy based on the sensed ECAP response and the one or more cardiac features of the cardiac signal. For example, IMD 102 may determine an appropriate adjustment to one or more electrical stimulation therapy parameters in order to achieve a target ECAP characteristic value. In some examples, a characteristic value of the ECAP signal may be compared to a target ECAP characteristic value (e.g., a numerical value for a characteristic or an ECAP signal template) corresponding to efficacious therapy.

As another example, IMD 102 may determine whether the cardiac features are indicative of increased pain in patient 112. For example, a decreasing HRV of patient 112 may be indicative that patient 112 is experiencing increased pain. In response, IMD 102 may increase a value of one or more electrical stimulation therapy parameters defining the SCS therapy so as to increase the efficacy of the SCS therapy provided to patient 112.

As another example, IMD 102 may determine whether the cardiac features are indicative of decreased pain in patient 112. For example, an increasing HRV of patient 112 may be indicative that patient 112 is experiencing decreased pain. In response, IMD 102 may decrease a value of one or more electrical stimulation therapy parameters defining the SCS therapy so as to decrease the power consumption of IMD 102 and thereby increase the battery longevity of IMD 102 where relatively stronger, and more power consuming, therapy programs are not needed to provide efficacious therapy to patient 112.

The following examples may illustrate one or more aspects of the disclosure.

Example 1: A method includes sensing, by an implantable medical device (IMD) and via a plurality of electrodes disposed on one or more leads implanted within an epidural space of a patient, an electrical signal; determining, by processing circuitry and from the electrical signal, one or more cardiac features indicative of activity of a heart of the patient; and controlling, by the processing circuitry and based on the one or more cardiac features, delivery of spinal cord stimulation (SCS) therapy to the patient.

Example 2: The method of example 1, wherein controlling delivery of the SCS therapy comprises adjusting, based on the one or more cardiac features, one or more parameters at least partially defining the SCS therapy.

Example 3: The method of example 2, further comprising delivering, by the IMD and via the plurality of electrodes, the SCS therapy according to the adjusted one or more parameters.

Example 4: The method of any of examples 1, wherein controlling, based on one or more cardiac features, delivery of the SCS therapy comprises: determining, by the processing circuitry, that the one or more cardiac features are indicative of a change in pain experienced by the patient; and controlling, by the processing circuitry and based on the determination that that the one or more cardiac features are indicative of the change in pain experienced by the patient, delivery of the SCS therapy.

Example 5: The method of example 1, wherein the one or more cardiac features comprise one or more of: a heart rate of the heart of the patient; a night time heart rate of the heart of the patient; a heart rate variability (HRV) of the heart of the patient; a root mean square of successive differences between normal heartbeats (RMSSD) of the heart of the patient; frequency domain information of the heart of the patient; a QRS width; a QT duration; or a PR interval.

Example 6: The method of example 5, wherein the one or more cardiac features comprise the HRV of the heart of the patient, and wherein controlling, based on one or more cardiac features, delivery of the SCS therapy comprises: determining, by the processing circuitry, that the HRV of the patient has decreased, wherein the decrease in HRV of the patient is indicative of an increase in pain experienced by the patient; and controlling, by the processing circuitry and based on the determination that the HRV of the patient has decreased, delivery of the SCS therapy.

Example 7: The method of example 1, further includes sensing, by the IMD and via the plurality of electrodes disposed on the one or more leads implanted within the epidural space of the patient, an evoked compound action potential (ECAP) of a tissue within the epidural space of the patient in response to the delivered SCS therapy, and adjusting, based on the one or more cardiac features and the sensed ECAP response, one or more parameters at least partially defining the SCS therapy.

Example 8: The method of example 1, wherein the one or more cardiac features comprise a heart rate variability (HRV) of the heart of the patient, and wherein controlling delivery of the SCS therapy comprises cycling, based on the HRV of the heart of the patient, the SCS therapy on and off.

Example 9: The method of example 1, wherein the one or more cardiac features comprise a heart rate variability (HRV) of the heart of the patient, and wherein controlling delivery of the SCS therapy comprises adjusting, based on the HRV of the heart of the patient, a duty cycle of the SCS therapy.

Example 10: The method of example 1, further includes sensing, via one or more sensors, a state of the patient; and wherein controlling delivery of the SCS therapy comprises: determining, by the processing circuitry and based on the one or more cardiac features and the state of the patient, a pain metric for the patient; and controlling, based on the pain metric for the patient, delivery of the SCS therapy.

Example 11: The method of example 1, wherein determining, from the electrical signal, the one or more cardiac features indicative of activity of the heart of the patient comprises applying, by the processing circuitry, a low-pass filter to the electrical signal to obtain the one or more cardiac features indicative of activity of the heart of the patient.

Example 12: The method of example 1, wherein the IMD comprises the processing circuitry.

Example 13: A medical device comprising processing circuitry configured to: receive an electrical signal sensed via a plurality of electrodes disposed on one or more leads implanted within an epidural space of a patient; determine, from the electrical signal, one or more cardiac features indicative of activity of a heart of the patient; and control, based on the one or more cardiac features, delivery of spinal cord stimulation (SCS) therapy to the patient.

Example 14: The medical device of example 13, wherein to control delivery of the SCS therapy, the processing circuitry is configured to adjust, based on the one or more cardiac features, one or more parameters at least partially defining the SCS therapy.

Example 15: The medical device of example 14, wherein the medical device is further configured to deliver, via the plurality of electrodes, the SCS therapy according to the adjusted one or more parameters.

Example 16: The medical device of example 13, wherein to control, based on one or more cardiac features, delivery of the SCS therapy, the processing circuitry is configured to: determine that the one or more cardiac features are indicative of a change in pain experienced by the patient; and control, based on the determination that that the one or more cardiac features are indicative of the change in pain experienced by the patient, delivery of the SCS therapy.

Example 17: The medical device of example 13, wherein the one or more cardiac features comprise one or more of: a heart rate of the heart of the patient; a night time heart rate of the heart of the patient; a heart rate variability (HRV) of the heart of the patient; a root mean square of successive differences between normal heartbeats (RMSSD) of the heart of the patient; frequency domain information of the heart of the patient; a QRS width; a QT duration; or a PR interval.

Example 18: The medical device of example 17, wherein the one or more cardiac features comprise the HRV of the heart of the patient, and wherein to control, based on one or more cardiac features, delivery of the SCS therapy, the processing circuitry is configured to: determine that the HRV of the patient has decreased, wherein the decrease in HRV of the patient is indicative of an increase in pain experienced by the patient; and control, based on the determination that the HRV of the patient has decreased, delivery of the SCS therapy.

Example 19: The medical device of example 13, wherein the processing circuitry is further configured to: receive an evoked compound action potential (ECAP) of a tissue within the epidural space of the patient sensed via the plurality of electrodes disposed on the one or more leads implanted within the epidural space of the patient in response to the delivered SCS therapy, and adjust, based on the one or more cardiac features and the sensed ECAP response, one or more parameters at least partially defining the SCS therapy.

Example 20: A system includes an implantable medical device includes a plurality of electrodes disposed on one or more leads configured for implantation within an epidural space of a patient; sensing circuitry configured to sense, via the plurality of electrodes, an electrical signal; and stimulation generation circuitry configured to deliver, via the plurality of electrodes, spinal cord stimulation (SCS) therapy to the patient; and processing circuitry configured to: determine, from the electrical signal, one or more cardiac features indicative of activity of a heart of the patient; and control, based on the one or more cardiac features, the stimulation generation circuitry to deliver the SCS therapy to the patient.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

Various examples have been described. These and other examples are within the scope of the following claims.

What is claimed is:

1. A method comprising:
    determining, by processing circuitry of an implantable medical device (IMD), that a patient is within one patient state of a plurality of patient states, wherein the patient state comprises at least one of a lying-down state or a sleep state;
    in response to the determination that the patient is within the patient at least one of the lying-down state or the sleep state, sensing, by the processing circuitry and via a plurality of electrodes disposed on one or more leads implanted within an epidural space of the patient, an electrical signal;
    obtaining, by the processing circuitry and from the electrical signal, one or more cardiac features indicative of activity of a heart of the patient during the at least one of the lying-down state or the sleep state; and
    controlling, by the processing circuitry, delivery of a spinal cord stimulation (SCS) signal to the patient via the plurality of electrodes based at least in part on the one or more cardiac features indicative of activity of the heart of the patient.

2. The method of claim 1, wherein controlling the delivery of the SCS signal to the patient comprises one of:
    enabling delivery of the SCS signal to the patient; or
    disabling delivery of the SCS signal to the patient.

3. The method of claim 1, wherein controlling the delivery of the SCS signal to the patient comprises:
    delivering the SCS signal to the patient;
    sensing an evoked compound action potential (ECAP) response of a tissue within the epidural space of the patient to the delivered SCS signal;
    adjusting, based on the sensed ECAP response, one or more parameters at least partially defining the SCS signal; and
    delivering the adjusted SCS signal to the patient.

4. The method of claim 1, wherein determining that the patient is within the patient state of the plurality of patient states comprises determining that the patient is within the lying-down state.

5. The method of claim 1, wherein determining that the patient is within the patient state of the plurality of patient states comprises determining that the patient is within the sleep state.

6. The method of claim 1, wherein determining that the patient is within the patient state of the plurality of patient states comprises:
    sensing, via an accelerometer of the IMD, an activity level of the patient; and
    determining, based on the sensed activity level of the patient, that the patient is within the patient state of the plurality of patient states.

7. The method of claim 1, wherein determining that the patient is within the patient state of the plurality of patient states comprises:
    sensing, via an accelerometer of the IMD, a movement of the patient;
    determining, based on the sensed movement of the patient, a posture of the patient; and
    determining, based on the determined posture of the patient, that the patient is within the patient state of the plurality of patient states.

8. The method of claim 1, wherein controlling delivery of the SCS signal to the patient based at least in part on the one or more cardiac features indicative of activity of the heart of the patient comprises:
    determining that the one or more cardiac features are indicative of a change in pain experienced by the patient; and
    in response to the determination that the one or more cardiac features are indicative of the change in pain experienced by the patient, controlling delivery of the SCS signal to the patient.

9. The method of claim 1, further comprising:
    determining, by the processing circuitry and based on the one or more cardiac features and a signal sensed by an accelerometer of the IMD, that a wash-in period of the SCS therapy has ended,
    wherein controlling the delivery of the SCS signal is based at least in part on (1) the one or more cardiac features indicative of activity of the heart of the patient and (2) the determination that the wash-in period of the SCS therapy has ended.

10. The method of claim 1, wherein the one or more cardiac features comprise one or more of:
    a heart rate of the heart of the patient;
    a night time heart rate of the heart of the patient;
    a heart rate variability (HRV) of the heart of the patient;
    a root mean square of successive differences between normal heartbeats (RMSSD) of the heart of the patient;
    frequency domain information of the heart of the patient;
    a QRS width;
    a QT duration; or
    a PR interval.

11. The method of claim 1,
    wherein the one or more cardiac features comprise a heart rate variability (HRV) of the heart of the patient, and
    wherein controlling the delivery of the SCS signal to the patient comprises:
        determining, while the IMD is not delivering the SCS signal, that the HRV of the patient has decreased, wherein the decrease in the HRV of the patient is indicative of an increase in pain experienced by the patient; and
        enabling, based on the determination that the HRV of the patient has decreased, delivery of the SCS signal.

12. An implantable medical device (IMD) comprising:
    a plurality of electrodes configured to be disposed on one or more leads implanted within an epidural space of a patient; and
    processing circuitry configured to:
        determine that a patient is within one patient state of a plurality of patient states, wherein the patient state comprises at least one of a lying-down state or a sleep state;

in response to the determination that the patient is within the at least one of the lying-down state or the sleep state, sense, via the plurality of electrodes, an electrical signal;

obtain, from the electrical signal, one or more cardiac features indicative of activity of a heart of the patient during the at least one of the lying-down state or the sleep state; and control delivery of a spinal cord stimulation (SCS) signal to the patient via the plurality of electrodes based at least in part on the one or more cardiac features indicative of activity of the heart of the patient.

13. The IMD of claim 12, wherein the processing circuitry is configured to control the delivery of the SCS signal to the patient by one of:

enabling delivery of the SCS signal to the patient; or disabling delivery of the SCS signal to the patient.

14. The IMD of claim 12, wherein to control the delivery of the SCS signal to the patient, the processing circuitry is configured to:

deliver the SCS signal to the patient;

sense an evoked compound action potential (ECAP) response of a tissue within the epidural space of the patient to the delivered SCS signal;

adjust, based on the sensed ECAP response, one or more parameters at least partially defining the SCS signal; and deliver the adjusted SCS signal to the patient.

15. The IMD of claim 12, wherein to determine that the patient is within the patient state of the plurality of patient states, the processing circuitry is configured to determine that the patient is within the lying-down state.

16. The IMD of claim 12, wherein to determine that the patient is within the patient state of the plurality of patient states, the processing circuitry is configured to determine that the patient is within the sleep state.

17. The IMD of claim 12, wherein the IMD further comprises an accelerometer, and wherein to determine that the patient is within the patient state of the plurality of patient states, the processing circuitry is configured to:

sense, via the accelerometer of the IMD, an activity level of the patient; and determine, based on the sensed activity level of the patient, that the patient is within the patient state of the plurality of patient states.

18. The IMD of claim 12, wherein the IMD further comprises an accelerometer, and wherein to determine that the patient is within the patient state of the plurality of patient states, the processing circuitry is configured to:

sense, via the accelerometer of the IMD, a movement of the patient;

determine, based on the sensed movement of the patient, a posture of the patient; and determine, based on the determined posture of the patient, that the patient is within the patient state of the plurality of patient states.

19. The IMD of claim 12, wherein the one or more cardiac features comprise one or more of:

a heart rate of the heart of the patient;

a night time heart rate of the heart of the patient;

a heart rate variability (HRV) of the heart of the patient;

a root mean square of successive differences between normal heartbeats (RMSSD) of the heart of the patient;

frequency domain information of the heart of the patient;

a QRS width;

a QT duration; or a PR interval.

20. A non-transitory, computer-readable medium comprising instructions that, when executed, are configured to cause processing circuitry of an implantable medical device (IMD) to:

determine that a patient is within one patient state of a plurality of patient states, wherein the patient state comprises at least one of a lying-down state or a sleep state;

in response to the determination that the patient is within the at least one of the lying-down state or the sleep state, sense, via a plurality of electrodes disposed on one or more leads implanted within an epidural space of the patient, an electrical signal;

obtain, from the electrical signal, one or more cardiac features indicative of activity of a heart of the patient during the at least one of the lying-down state or the sleep state; and control delivery of a spinal cord stimulation (SCS) signal to the patient via the plurality of electrodes based at least in part on the one or more cardiac features indicative of activity of the heart of the patient.

* * * * *